(12) United States Patent
Liao et al.

(10) Patent No.: US 8,940,506 B2
(45) Date of Patent: Jan. 27, 2015

(54) HIGH-SENSITIVE FLUORESCENT ENERGY TRANSFER ASSAY USING FLUORESENT AMINO ACIDS AND FLUORESCENT PROTEINS

(75) Inventors: Jiayu Liao, Carlsbad, CA (US); Yang Song, Riverside, CA (US); Yongfeng Zhao, Riverside, CA (US); Yan Liu, Riverside, CA (US)

(73) Assignee: The Regents of the University of California, Oakland, CA (US)

( * ) Notice: Subject to any disclaimer, the term of this patent is extended or adjusted under 35 U.S.C. 154(b) by 163 days.

(21) Appl. No.: 12/933,780

(22) PCT Filed: Mar. 21, 2009

(86) PCT No.: PCT/US2009/037907
§ 371 (c)(1),
(2), (4) Date: Jan. 18, 2011

(87) PCT Pub. No.: WO2009/117726
PCT Pub. Date: Sep. 24, 2009

(65) Prior Publication Data
US 2011/0117556 A1    May 19, 2011

Related U.S. Application Data

(60) Provisional application No. 61/038,526, filed on Mar. 21, 2008, provisional application No. 61/098,722, filed on Sep. 19, 2008.

(51) Int. Cl.
*G01N 33/68* (2006.01)
*C12Q 1/68* (2006.01)
*C07K 14/00* (2006.01)
*C07K 19/00* (2006.01)
*G01N 33/542* (2006.01)

(52) U.S. Cl.
CPC .................................. *G01N 33/542* (2013.01)
USPC ............... 435/86; 435/6.1; 435/7.1; 530/300; 530/350

(58) Field of Classification Search
USPC ................ 435/6.1, 7.1; 530/300, 350; 436/86
See application file for complete search history.

(56) References Cited

U.S. PATENT DOCUMENTS 6,335,201 B1 * 1/2002 Allbritton et al. ............... 436/63
6,600,017 B1 * 7/2003 Glabe et al. .................... 530/345

2005/0233389 A1   10/2005 Ting et al.
2006/0063244 A1   3/2006 Schultz et al.
2000/8004488     2/2008 Wang et al.

FOREIGN PATENT DOCUMENTS

WO    2006110182 A2    10/2006
WO    2007059312 A2    5/2007
WO    2007090198 A2    8/2007

OTHER PUBLICATIONS

Vogt, Titus. Supplementary European Search Report. European Application No. 09723144. Date of completion of search: Feb. 2, 2012.
Fernandez, Fabio et al. "Quantification of Protein-Lipid Selectivity using FRET: Application to the M13 Major Coat Protein", Biophysical Journal, vol. 87, pp. 344-352, Jul. 2004.
Rodriguez, Erik A. et al., "In vivo incorporation of multiple unnatural amino acids through nonsense and frameshift suppression", PNAS, vol. 103, No. 23, Jun. 6, 2006.
Stromgaard, Anne et al., "Site Specific Incorporation of Unnatural Amino Acids into Proteins", ChemBioChem, 2004, vol. 5, pp. 909-916.
Turcatti, Gerardo et al. "Probing the Structure and Function of the Tachykinin Neurokinin-2 Receptor through Biosynthetic Incorporation of Fluorescent Amino Acids at Specific Sites", The Journal of Biological Chemistry, vol. 271, No. 33, Aug. 16, 1996, pp. 19991-19998.
Hohsaka et al., "Incorporation of non-natural amino acids into proteins," Curr. Opin. Chem. Biol., Dec. 2002, pp. 809-815, vol. 6, No. 6.
Shin, Weon Hye, International Search Report and Written Opinion, PCT/US2009/037907, Nov. 2, 2009, Korean Intellectual Property Office.
Sui et al., "Synthesis of a coumarin based fluorescent amino acid," Letters in Peptide Science, Jan. 2001, pp. 47-51, vol. 8, No. 1.
Taki et al., "Position-specific incorporation of a fluorophore-quencher pair into a single streptavidin through orthogonal four-base codon/anticondon pairs," J. Am. Chem Soc., Dec. 2002, pp. 14586-14590, vol. 124, No. 49.
Zhang et al., "Fluorescent detection of peptides an amino acids for capillary electrophoresis via on-line derivatization with 4-fluoro-7-nitro-2,1,3-benzoxadiazole," Analytical and Bioanalytical Chemistry, Nov. 2006, pp. 1387-1394, vol. 386, No. 5.

\* cited by examiner

*Primary Examiner* — Chih-Min Kam
(74) *Attorney, Agent, or Firm* — Joseph R. Baker, Jr.; Gavrilovich, Dodd & Lindsey LLP

(57) ABSTRACT

The disclosure provides method and composition utilizing fluorescent amino acids and endogenous fluorescent proteins comprising a moiety capable of undergoing FRET. The methods and compositions of the disclosure are useful in analyzing protein structure and function, and screening molecular inhibitors.

11 Claims, 16 Drawing Sheets

Box A and B:
consensus internal
promoter sequences
CUA(34-36):
trinucleotide
anticodon
5' flanking
sequence of human
tRNATyr is added to
ensure the
expression in
mammalian cells 5 amino acid
residues
randomly
mutated to
generate mutant
library: Tyr37,
Asn126, Asp182,
Phe183, Leu186

Efficiency: expression level of amber mutated luciferase vs. wt luciferase

Specificity: expression of amber mutated luciferase in the absense of BstRNA$^{Tyr}_{CUA}$/EcTyrRS or uAA

HIGH-SENSITIVE FLUORESCENT ENERGY TRANSFER ASSAY USING FLUORESENT AMINO ACIDS AND FLUORESCENT PROTEINS

CROSS REFERENCE TO RELATED APPLICATIONS

This application claims priority under 35 U.S.C. §119 to U.S. Provisional Application No. 61/038,526, filed Mar. 21, 2008, and U.S. Provisional Application No. 61/098,722, filed Sep. 19, 2008, the disclosures of which are incorporated herein by reference.

FIELD OF THE INVENTION

The disclosure relates to the field of protein biochemistry and protein analysis. More particularly, the disclosure relates to the field of compositions and methods for producing proteins that include fluorescent amino acids or fluorescent proteins and using such fluorescent amino acids or fluorescent proteins in FRET analyses or protein-protein or amino acid-amino acid, or amino acid-protein interactions, or high-throughput screenings.

BACKGROUND

Proteins carry out virtually all of the complex processes of life. Accordingly, understanding their structure, function and interactions with the environment provide information useful in the development of diagnostic, prognostics, therapies and the like.

SUMMARY

The disclosure provides peptides, polypeptides, proteins, or any other composition comprising at least two fluorescent amino acids or two fluorophores that are capable of undergoing FRET, wherein one of the amino acids comprises a fluorophore and one comprises a quencher of the FRET signal when placed in close proximity to the fluorophore. In one embodiment, the peptide, polypeptide protein or composition comprises a first fluorescent amino acid comprising a quencher amino acid having a general structure I:

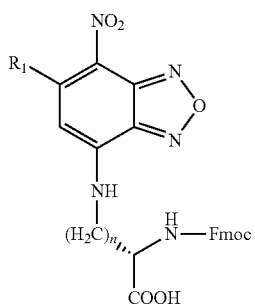

(I)

wherein n is any integer between 1 and 10 inclusive (e.g., 1, 2, 3, 4, 5 etc.) and $R_1$ is selected from the group consisting of: H, aryl, substituted aryl, alkyl, substituted alkyl, carboxyl, aminocarbonyl, alkylsulfonylaminocarboxyl, alkoxycarbonyl, and halo.

In yet a further embodiment, the composition further contains a fluorophore amino acid having a general structure II:

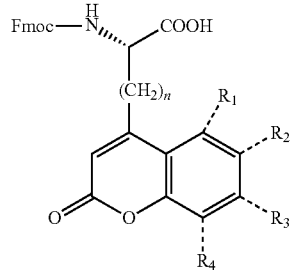

(II)

wherein n is any integer between 1 and 10 inclusive (e.g., 1, 2, 3, 4, 5 etc.) and $R_1$ is selected from the group consisting of: H, aryl, substituted aryl, alkyl, substituted alkyl, carboxyl, aminocarbonyl, alkylsulfonylaminocarboxyl, alkoxycarbonyl, and halo, or $R_1$ and $R_2$, together with the carbons to which they are bound, can be joined to form a 4 to 7 membered ring or a substituted 4 to 7 membered ring; $R_2$ is selected from the group consisting of: H, aryl, substituted aryl, alkyl, substituted alkyl, carboxyl, aminocarbonyl, alkylsulfonylaminocarboxyl, alkoxycarbonyl, and halo, or $R_2$ and $R_1$, together with the carbons to which they are bound, can be joined to form a 4 to 7 membered ring or a substituted 4 to 7 membered ring, or $R_2$ and $R_3$, together with the carbons to which they are bound, can be joined to form a 4 to 7 membered ring or a substituted 4 to 7 membered ring; $R_3$ is selected from the group consisting of: H, aryl, substituted aryl, alkyl, substituted alkyl, carboxyl, aminocarbonyl, alkylsulfonylaminocarboxyl, alkoxycarbonyl, and halo, or $R_3$ and $R_2$, together with the carbons to which they are bound, can be joined to form a 4 to 7 membered ring or a substituted 4 to 7 membered ring, or $R_3$ and $R_4$, together with the carbons to which they are bound, can be joined to form a 4 to 7 membered ring or a substituted 4 to 7 membered ring; $R_4$ is selected from the group consisting of: H, aryl, substituted aryl, alkyl, substituted alkyl, carboxyl, aminocarbonyl, alkylsulfonylaminocarboxyl, alkoxycarbonyl, and halo, or $R_4$ and $R_3$, together with the carbons to which they are bound, can be joined to form a 4 to 7 membered ring or a substituted 4 to 7 membered ring. In yet another embodiment, the fluorescent amino acid comprises a general structure III:

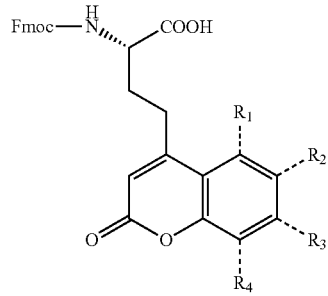

(III)

wherein $R_1$ is selected from the group consisting of: H, aryl, substituted aryl, alkyl, substituted alkyl, carboxyl, aminocarbonyl, alkylsulfonylaminocarboxyl, alkoxycarbonyl, and halo, or $R_1$ and $R_2$, together with the carbons to which they are bound, can be joined to form a 4 to 7 membered ring or a substituted 4 to 7 membered ring; $R_2$ is selected from the group consisting of: H, aryl, substituted aryl, alkyl, substituted alkyl, carboxyl, aminocarbonyl, alkylsulfonylaminocarboxyl, alkoxycarbonyl, and halo, or $R_2$ and $R_1$, together with the carbons to which they are bound, can be joined to form a 4 to 7 membered ring or a substituted 4 to 7 membered ring, or $R_2$ and $R_3$, together with the carbons to which they are bound, can be joined to form a 4 to 7 membered ring or a substituted 4 to 7 membered ring; $R_3$ is selected from the group consisting of: H, aryl, substituted aryl, alkyl, substituted alkyl, carboxyl, aminocarbonyl, alkylsulfonylaminocarboxyl, alkoxycarbonyl, and halo, or $R_3$ and $R_2$, together with the carbons to which they are bound, can be joined to form a 4 to 7 membered ring or a substituted 4 to 7 membered ring, or $R_3$ and $R_4$, together with the carbons to which they are bound, can be joined to form a 4 to 7 membered ring or a substituted 4 to 7 membered ring; $R_4$ is selected from the group consisting of: H, aryl, substituted aryl, alkyl, substituted alkyl, carboxyl, aminocarbonyl, alkylsulfonylaminocarboxyl, alkoxycarbonyl, and halo, or $R_4$ and $R_3$, together with the carbons to which they are bound, can be joined to form a 4 to 7 membered ring or a substituted 4 to 7 membered ring. In a specific embodiment, the fluorescent amino acid comprises a coumarin fluorescent amino acid comprising the structure IV:

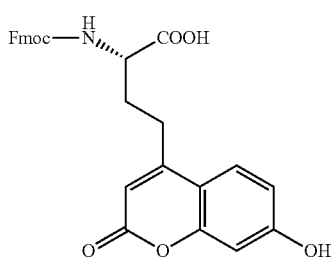

and a quenching NBD fluorescent amino acid comprising the general structure V:

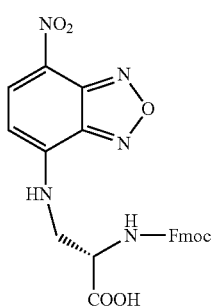

In yet another embodiment, the composition comprises a sequence containing a structure selected from I or V within about 1-15 (e.g., 1-10 nm, 2-8 nm etc.) of a fluorescent amino acid selected from the group consisting of II, III, or IV. In yet another embodiment, the fluorescent amino acid and quencher amino acid are spaced about 2, 3, 4, 5, 6, 7, 8, 9, or 10 amino acids from each other.

The disclosure provides a method of identifying a binding ligand or substrate for a target polypeptide comprising: providing a polynucleotide comprising at least one codon that results in the incorporation of at least one chromophore or fluorescent amino acid upon translation, wherein the chromophore or fluorescent amino acid comprises a first acceptor or donor chromophore or fluorophore moiety; translating the polynucleotide to obtain a labeled polypeptide comprising the at least one chromophore or fluorescent amino acid; contacting labeled polypeptide with a putative binding ligand comprising a second acceptor or donor chromophore or fluorophore moiety, wherein the first and second acceptor or donor chromophore or fluorophore moieties are different, wherein the first and second acceptor or donor chromophore or fluorophore moieties are selected to undergo Förster resonance energy transfer (FRET) when a binding ligand is bound to a target polypeptide, and identifying FRET, wherein the presence of FRET is indicative that the putative binding ligand binds to the target polypeptide thereby identifying the binding ligand. In one embodiment, the method is carried out in a cell-free system. In another embodiment, the method is carried out in a cell. In yet another embodiment, the acceptor is a quenching moiety. In yet a further embodiment, a first polypeptide comprises a fluorescent amino acid having the general structure II, II, or IV and second polypeptide comprises a fluorescent amino acid having the general structure I or V.

The disclosure also provides a method of identifying a structure of a polypeptide comprising: providing a polynucleotide comprising at least two codons that results in the incorporation of at least two chromophore or fluorescent amino acid upon translation, wherein the chromophore or fluorescent amino acid; translating the polynucleotide to obtain a labeled polypeptide comprising the at least two chromophore or fluorescent amino acid comprising at least a first and second chromophore or fluorophore moieties, wherein the first and second acceptor or donor chromophore or fluorophore moieties are different, wherein the first and second acceptor or donor chromophore or fluorophore moieties are selected to undergo Förster resonance energy transfer (FRET), and identifying FRET, wherein the presence of FRET is indicative that the at least two amino acids are within a selected distance from one another, thereby providing a structure of the polypeptide. In one embodiment, the method is carried out in a cell-free system. In another embodiment, the method is carried out in a cell. In yet another embodiment, the acceptor is a quenching moiety.

The fluorophore pairs of the disclosure can be used in combination with nucleic acids, lipids and other biological molecules in addition to proteins and polypeptide. Furthermore, the fluorophore pairs can be used in combination with solid substrates (e.g., tissue culture plate, beads, slides, nanoparticles and the like).

The disclosure also provide a method of identify protein-protein interactions in living cells.

The disclosure also provides a method of identifying molecules that inhibit the cleavage of peptide flanking by the fluorescent amino acids.

The disclosure also provides a method of identifying molecules that disrupt the protein-protein interaction in living cells.

The disclosure also provide the use of an NBD or NBD derivative and coumarin or coumarin derivative as fluorophores bound to substrates including bead, solid surface and biological compounds including nucleic acids, lipids and the like.

DETAILED DESCRIPTION

Figure 1:
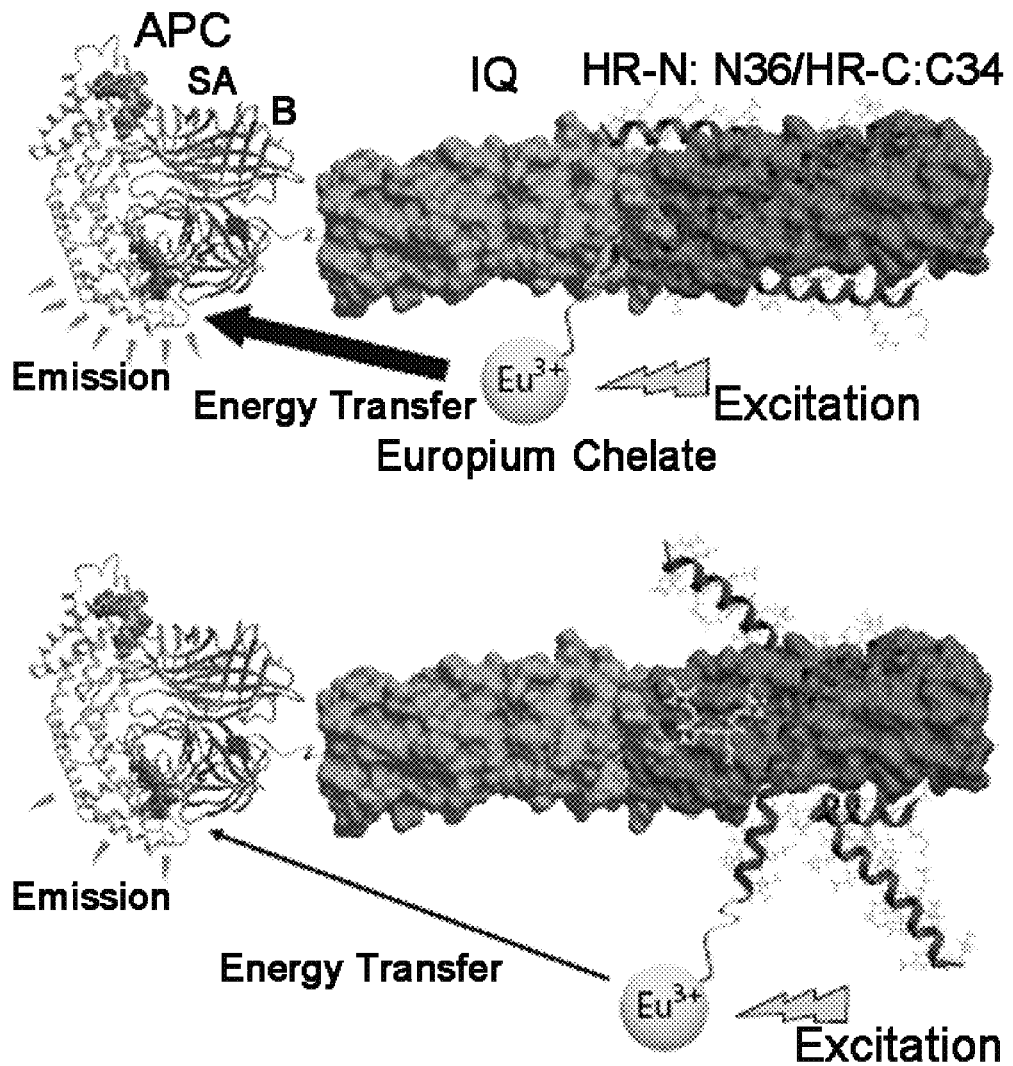
FIG. 1 depicts an exemplary methodology of the disclosure.
Figure 2:
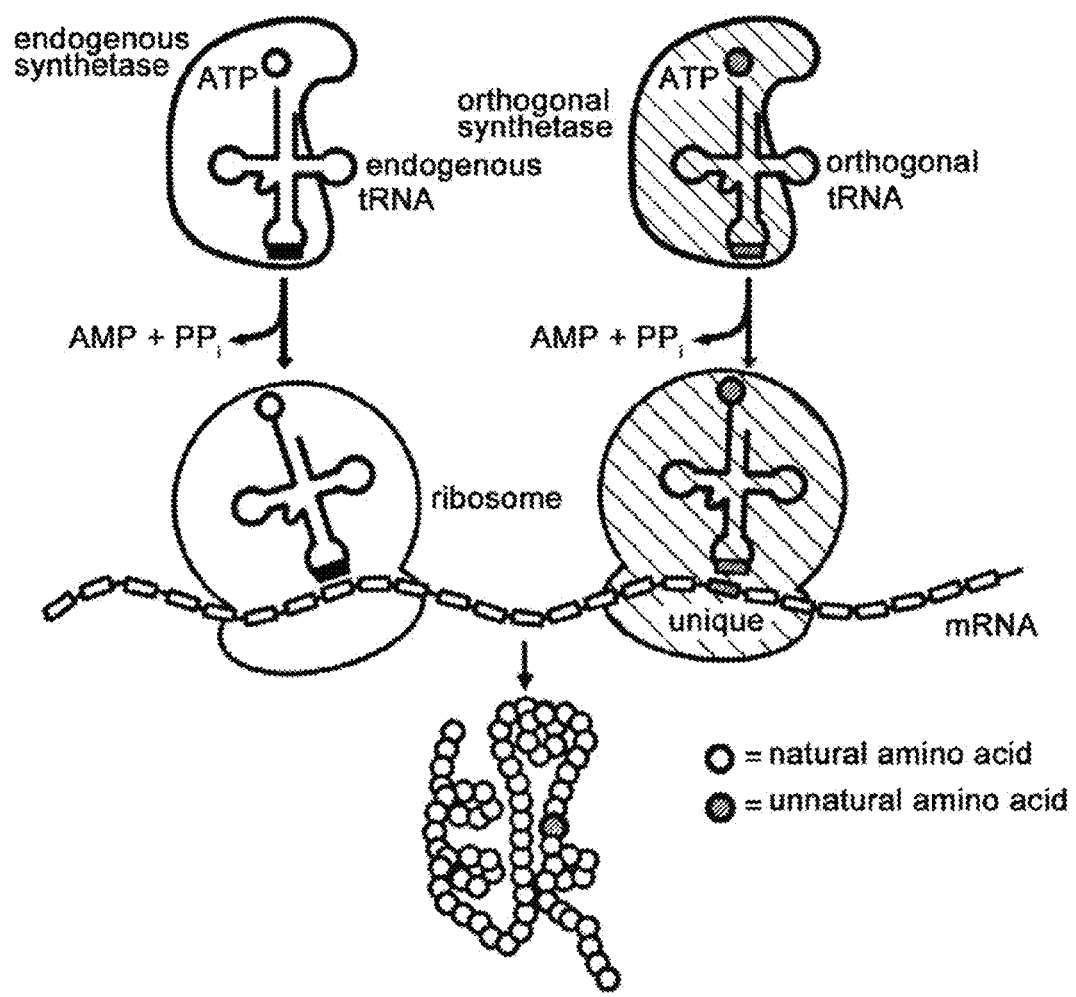
FIG. 2 depicts a process of incorporating fluorescent amino acids into a polypeptide.
Figure 3A:
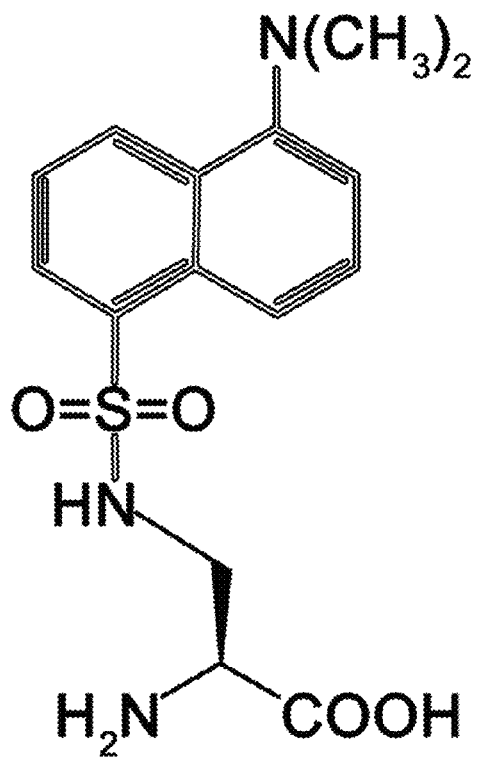
FIG. 3A-B depicts the structures of fluorescent amino acids and derivatives. (B) Structures of NBD (left) and CUM (right) fluorescent amino acids.
Figure 3B:
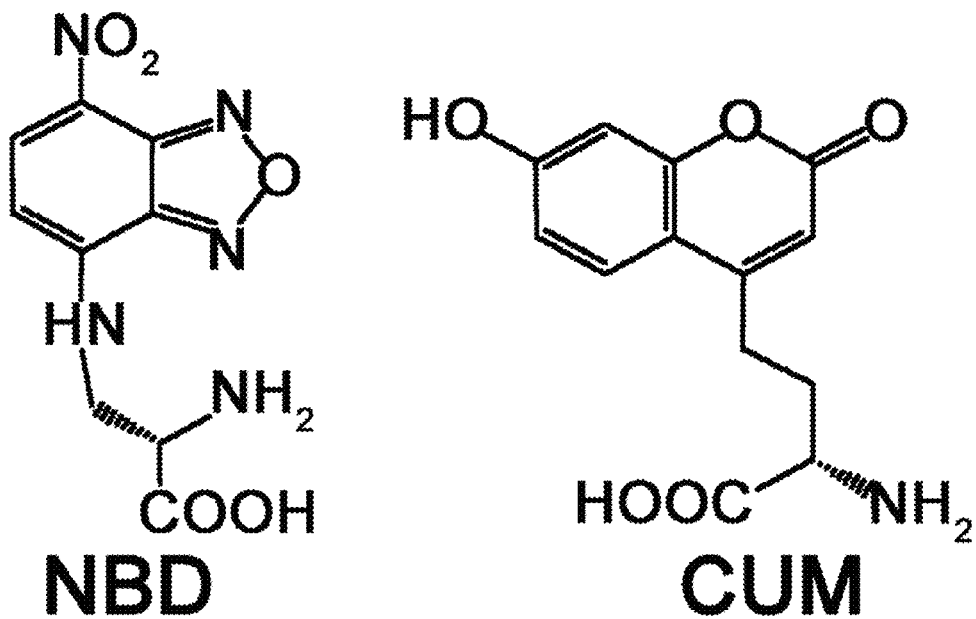

As used herein and in the appended claims, the singular forms "a," "and," and "the" include plural referents unless the context clearly dictates otherwise. Thus, for example, reference to "an fluorescent amino acid" includes a plurality of such fluorescent amino acids and reference to "the protein" includes reference to one or more proteins, and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Although methods and materials similar or equivalent to those described herein can be used in the practice of the disclosed methods and compositions, the exemplary methods, devices and materials are described herein.

Unless defined otherwise, all technical and scientific terms used herein have the same meaning as commonly understood to one of ordinary skill in the art to which this disclosure belongs. Thus, as used throughout the instant application, the following terms shall have the following meanings.

The phenomenon that Förster resonance energy transfer (FRET) occurs between a fluorophore and either (i) a second fluorophore with and overlapping emission-excitation spectrum or (ii) a quenching moiety that absorbs at the emission spectrum of the first fluorophore is useful for studying biological conditions. Such techniques have been used extensively in biological research to study protein conformational changes, protein interactions, intracellular signaling pathways, and discover novel biological bioactive chemicals for drug development. Typically, one fluorophore serves as an emitter and the second fluorophore serves as a quencher. During typical FRET assays one of the fluorophores is excited by an external excitation wavelength to induce fluorescence, the emitted spectrum from the first fluorophore will be absorbed by the second, quenching, fluorophore provide a distinct excitation emission spectrum. Where a change in the distance between the two fluorophores occurs, the excitation of the second fluorophore is modulated and thus provides a second distinctive excitation emission spectrum. This change in excitation-emission spectrums during a FRET assay is indicative of a biological effect, event or structure. However, in these systems the bulky size of traditional fluorophores used in FRET-based assays, e.g., the green fluorescent protein (GFP) variants, result in spatial hindrance and interference.

The disclosure uses fluorescent amino acid with side chain groups which can be genetically encoded and incorporated into peptides, polypeptide or proteins with high specificity to measure protein function and structure. Alternatively, and as described more thoroughly elsewhere herein, the amino acids may be incorporated into a desired peptide or polypeptide using standard peptide synthesis techniques.

The use of fluorescent amino acids has been described, however, proper quencher and emitter FRET pairs have not been identified. The use of a FRET pair of fluorescent amino acid provides the ability to measure biological and physical properties of peptide, polypeptide and proteins. Using the FRET pairs described herein a FRET reporter molecule with fluorescent amino acids can be used to facilitate the high-throughput screening of, for example, SUMO ligase and protease inhibitors or activity, which will be important in studies of cytokine signaling pathways, protein folding, protease activity and ligand binding pairs. The utilization of fluorescent amino acids in FRET-based high-throughput screening is a novel method to prevent the drawbacks of GFP variants, and it will broaden the application of fluorescent amino acids in biological research.

An "amino acid" is a molecule having the structure wherein a central carbon atom (the -carbon atom) is linked to a hydrogen atom, a carboxylic acid group (the carbon atom of which is referred to herein as a "carboxyl carbon atom"), an amino group (the nitrogen atom of which is referred to herein as an "amino nitrogen atom"), and a side chain group, R. When incorporated into a peptide, polypeptide, or protein, an amino acid loses one or more atoms of its amino acid carboxylic groups in the dehydration reaction that links one amino acid to another. As a result, when incorporated into a protein, an amino acid is referred to as an "amino acid residue."

An fluorescent amino acid comprises a structure wherein a central carbon atom is linked to a hydrogen atom, a carboxylic acid group (the carbon atom of which is referred to herein as a "carboxyl carbon atom"), an amino group (the nitrogen atom of which is referred to herein as an "amino nitrogen atom"), and a side chain group, R, wherein the R group is any substituent other than one used in the twenty natural amino acids. See, e.g., Biochemistry by L. Stryer, 3rd ed. 1988, Freeman and Company, New York, for structures of the twenty natural amino acids. Because the fluorescent amino acids typically differ from the natural amino acids in side chain only, the fluorescent amino acids form amide bonds with other amino acids, e.g., natural or unnatural, in the same manner in which they are formed in naturally occurring proteins. However, the fluorescent amino acids have side chain groups that distinguish them from the natural amino acids.

A fluorescent amino acid refers to a chemical compound comprising the general structure of an amino acid comprising, however, a non-naturally occurring chemical group(s). Examples of fluorescent amino acids include, but are not limited to, an fluorescent analogue of a tyrosine amino acid; an fluorescent analogue of a glutamine amino acid; an fluorescent analogue of a phenylalanine amino acid; an fluorescent analogue of a serine amino acid; an fluorescent analogue of a threonine amino acid; an alkyl, aryl, acyl, azido, cyano, halo, hydrazine, hydrazide, hydroxyl, alkenyl, alkynl, ether, thiol, sulfonyl, seleno, ester, thioacid, borate, boronate, phospho, phosphono, phosphine, heterocyclic, enone, imine, aldehyde, hydroxylamine, keto, or amino substituted amino acid, or any combination thereof; an amino acid with a photoactivatable cross-linker; a spin-labeled amino acid; a fluorescent amino acid; an amino acid with a novel functional group; an amino acid that covalently or noncovalently interacts with another molecule; a metal binding amino acid; a metal-containing amino acid; a radioactive amino acid; a photocaged and/or photoisomerizable amino acid; a biotin or biotin-analogue containing amino acid; a glycosylated or carbohydrate modified amino acid; a keto containing amino acid; amino acids comprising polyethylene glycol or polyether; a heavy atom substituted amino acid; a chemically cleavable or photocleavable amino acid; an amino acid with an elongated side chain; an amino acid containing a toxic group; a sugar substituted amino acid, e.g., a sugar substituted serine or the like; a carbon-linked sugar-containing amino acid; a redox-active amino acid; an α-hydroxy containing acid; an amino thio acid containing amino acid; an α,α disubstituted amino acid; a β-amino acid; and a cyclic amino acid other than proline.

Exemplary fluorescent amino acids include, but are not limited to, L-2-amino-3-(6,7-dimethoxy-4-coumaryl)-propionic acid (L-Adp); L-(7-hydroxycoumarin-4-yl)ethylglycine; β-pyrenylalanine (Pya); β-anthraniloyl-L-α,β-diaminopropionic acid (atn Dap) and its derivatives; β-[2-(phenyl) benzoxazol-5-yl]alanine derivatives (Box Ala); 4-ethoxymethylene-2-[1]naphtyl-5(4H)oxazolone derivatives; coumaryl amino acids such as (6,7-dimethoxy-4-coumaryl)alanine (Dmca), (6-methoxy-4-coumaryl)alanine (Mca), L-(7-hydroxy-4-coumaryl)alanine, L-(7-methoxy-4-coumaryl)alanine, D-(7-methoxy-4-coumaryl)alanine, L-(6-chloro, 7-hydroxy-4-coumaryl)alanine, L-(7-ethoxy-4-coumaryl)alanine, L-(5-methoxy, 7-hydroxy-4-coumaryl)alanine, L-(5,7-dimethoxy-4-coumaryl)alanine, L-(5,7-dihydroxy-4-coumaryl)alanine, L-(6,7-dimethoxy-4-coumaryl)alanine, L-(5-hydroxy, 7-methoxy-4-coumaryl) alanine, and L-(7-methoxy-4-coumaryl)ethylglycine (CUM).

"Protein" or "polypeptide" refers to any polymer of two or more individual amino acids (whether or not naturally occurring) linked via a peptide bond, and occurs when the carboxyl carbon atom of the carboxylic acid group bonded to the -carbon of one amino acid (or amino acid residue) becomes covalently bound to the amino nitrogen atom of amino group bonded to the -carbon of an adjacent amino acid. The term "protein" is understood to include the terms "polypeptide" and "peptide" (which, at times may be used interchangeably herein) within its meaning. In addition, proteins comprising multiple polypeptide subunits (e.g., DNA polymerase III, RNA polymerase II) or other components (for example, an RNA molecule, as occurs in telomerase) will also be understood to be included within the meaning of "protein" as used herein. Similarly, fragments of proteins and polypeptides are also within the scope of the invention and may be referred to herein as "proteins."

A particular amino acid sequence of a given protein (i.e., the polypeptide's "primary structure," when written from the amino-terminus to carboxy-terminus) is determined by the nucleotide sequence of the coding portion of a mRNA, which is in turn specified by genetic information, typically genomic DNA (including organelle DNA, e.g., mitochondrial or chloroplast DNA). Thus, determining the sequence of a gene assists in predicting the primary sequence of a corresponding polypeptide and more particular the role or activity of the polypeptide or proteins encoded by that gene or polynucleotide sequence.

"Polynucleotide" or "nucleic acid sequence" refers to a polymeric form of nucleotides. In some instances a polynucleotide refers to a sequence that is not immediately contiguous with either of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides of the invention can be ribonucleotides, deoxyribonucleotides, or modified forms of either nucleotide. A polynucleotides as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions.

"Isolated polypeptide" refers to a polypeptide which is separated from other contaminants that naturally accompany it, e.g., protein, lipids, and polynucleotides. The term embraces polypeptides which have been removed or purified from their naturally-occurring environment or expression system (e.g., host cell or in vitro synthesis).

"Substantially pure polypeptide" refers to a composition in which the polypeptide species is the predominant species present (i.e., on a molar or weight basis it is more abundant than any other individual macromolecular species in the composition), and is generally a substantially purified composition when the object species comprises at least about 50 percent of the macromolecular species present by mole or % weight. Generally, a substantially pure polypeptide composition will comprise about 60% or more, about 70% or more, about 80% or more, about 90% or more, about 95% or more, and about 98% or more of all macromolecular species by mole or % weight present in the composition. In some embodiments, the object species is purified to essential homogeneity (i.e., contaminant species cannot be detected in the composition by conventional detection methods) wherein the composition consists essentially of a single macromolecular species. Solvent species, small molecules (<500 Daltons), and elemental ion species are not considered macromolecular species.

"Förster resonance energy transfer" or "FRET" occurs when excitation energy is transferred between a donor chromophore (or fluorophore) that has absorbed a photon and an acceptor moiety, causing quenching of donor electromagnetic radiation elicited from the donor chromophore (or fluorophore). If the acceptor moiety is a chromophore (or fluorophore) whose excitation spectra overlaps with the emissions spectra of the donor, the acceptor moiety will emit electromagnetic radiation at its characteristic emissions wavelength. If the acceptor moiety is a not a chromophore (or fluorophore), it will quench the electromagnetic radiation of the donor chromophore (or fluorophore) without emitting any of its own electromagnetic radiation. In this case the acceptor moiety is a chromophore (or fluorophore) quencher.

As used herein, a "donor chromophore (or fluorophore)" is a chromophore (or fluorophore) that, upon absorbing light or other energy, can transfer excitation energy to an acceptor chromophore (or fluorophore) or a chromophore (or fluorophore) quencher. This energy transfer can occur when the absorption spectrum of an acceptor chromophore (or fluorophore) overlaps the emissions spectrum of the donor chromophore (or fluorophore). These changes in emission either by the donor or a combination of the donor and acceptor can be detected using various known detection methods (e.g., fluorescent cameras, luminescence, light absorbing materials, CCD cameras and the like). In one aspect, an fluorescent amino acid comprises a chromophore (or fluorophore) moiety. In yet another aspect, a polypeptide comprises at least one fluorescent amino acid comprising a donor chromophore (or fluorophore) and at least one fluorescent amino acid comprising an acceptor or quencher chromophore (or fluorophore).

A "FRET pair" refers to a donor chromophore (or fluorophore) moiety and an acceptor chromophore (or fluorophore) moiety, where the donor, when exposed to an appropriate excitation wavelength, can transfer excitation energy to the acceptor moiety. This process is dependent on the distance between donor and acceptor moieties or a donor and a quencher moiety and requires that the absorption spectrum of the acceptor or quencher overlaps the emissions spectrum of the donor. The two members of a FRET pair can be referred to as a FRET pair.

As the distance changes between a FRET pair the emission spectra changes. Typically, a FRET pair are capable of effecting one another when the distance between them are between about 10 and 80 nm, typically about 10-50, and most commonly about 20-30 nm. As the distance between the FRET pair increases the drop in the emission wavelength of an acceptor moiety will be reduced or the emission spectra of the donor (where the acceptor is a quencher) will increase. Accordingly, using such changes in emission spectra one can determine distances between, for example, an amino acid in a single polypeptide or the distances between an amino acid in a polypeptide and one in a binding ligand, substrate or the like. In this way, inhibitors that bind to a particular target site on a polypeptide can be detected using changes in emission spectra.

As mentioned above, the efficiency of FRET is dependent on the separation distance and the orientation of the donor and acceptor moieties, as described by the Forster equation, the fluorescent quantum yield of the donor moiety and the energetic overlap with the acceptor moiety. Forster derived the relationship: $E=(F^0-F)/F^0=R_0^6/(R^6+R_0^6)$, where E is the efficiency of FRET, F and $F^0$ are the fluorescence intensities of the donor in the presence and absence of the acceptor, respectively, and R is the distance between the donor and the acceptor. $R_0$, the distance at which the energy transfer efficiency is 50%, is given (nm) by $R_0=9.79\times10^3(K^2QJn^{-4})^{1/6}$, where $K^2$ is an orientation factor having an average value close to 0.67 for freely mobile donors and acceptors, Q is the quantum yield of the unquenched fluorescent donor, n is the refractive index of the intervening medium, and J is the overlap integral, which expresses in quantitative terms the degree of spectral overlap, $$J = \int \bullet_0 \varepsilon_\lambda F_\lambda \lambda^4 d\lambda \Big/ \int \bullet_0 F_\lambda d\lambda$$

where $\varepsilon_\lambda$ is the molar absorptivity of the acceptor in $M^{-1}$ $cm^{-1}$ and $F_\lambda$ is the donor fluorescence at wavelength 1 measured in cm. Forster, T. (1948) Ann. Physik 2:55-75. Tables of spectral overlap integrals are readily available to those working in the field (for example, Berlman, I. B. Energy transfer parameters of aromatic compounds, Academic Press, New York and London (1973)).

The characteristic distance $R_0$ at which FRET is 50% efficient depends on the quantum yield of the donor i.e., the shorter-wavelength fluorophore, the extinction coefficient of the acceptor, i.e., the longer-wavelength fluorophore, and the overlap between the donor's emission spectrum and the acceptor's excitation spectrum.

Accordingly, Forster resonance energy transfer (FRET) occurs between two adjacent fluorophores when their distance is small (e.g., 1-10 nm) and the emission spectrum of one fluorophore has more than 30% overlapping with the excitation spectrum of the other. FRET results in the quenching of the donor fluorophore and excitation of the acceptor fluorophore. Because the efficiency of energy transfer is highly dependent (sixth-power) on the distance between donor and acceptor fluorophores, FRET-based techniques have been extensively used in biological research including identification of protein interactions, real-time monitoring of intracellular signaling activities, and high-throughput screening of bioactive chemicals. The green fluorescent protein (GFP) variants are the most commonly used fluorophores to label the target proteins in FRET-based assays and they are powerful probes for protein localizations and interactions. However, the fluorescent protein also possesses certain disadvantages. The labeling is limited to the N- or C-terminus of target proteins, and the bulky size of these fluorescent proteins sometimes interferes with the normal function of target proteins because of spatial hindrance. In terms of FRET-based assays, the flexibility of fluorescent protein labels also desensitizes the detection of the change of donor-acceptor distance. Fluorescent amino acids offer unique advantages in that it not only can they be incorporated into proteins in a highly specific manner but the rigidity of their small side chain groups also enhances the sensitivity of FRET-based assays without perturbing protein functions.

The disclosure provides peptides, polypeptide or proteins comprising at least two fluorescent amino acids that are capable of undergoing FRET. In one embodiment, the peptide, polypeptide or protein comprises a first fluorescent amino acid comprising a coumarin fluorescent amino acid and a quencher amino acid having a general structure I:

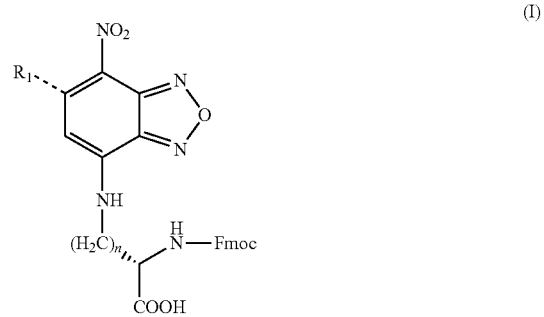

(I)

wherein n is any integer between 1 and 10 inclusive (e.g., 1, 2, 3, 4, 5 etc.) and $R_1$ is selected from the group consisting of: H, aryl, substituted aryl, alkyl, substituted alkyl, carboxyl, aminocarbonyl, alkylsulfonylaminocarboxyl, alkoxycarbonyl, and halo. In yet a further embodiment, the coumarin fluorescent amino acid has a general structure II:

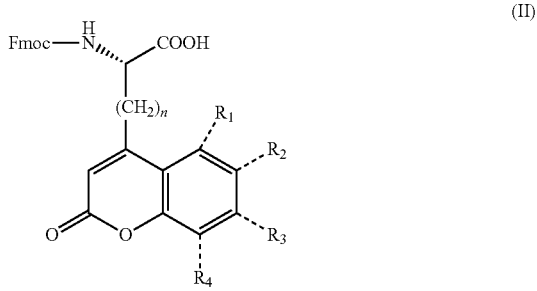

(II)

wherein n is any integer between 1 and 10 inclusive (e.g., 1, 2, 3, 4, 5 etc.) and $R_1$ is selected from the group consisting of: H, aryl, substituted aryl, alkyl, substituted alkyl, carboxyl, aminocarbonyl, alkylsulfonylaminocarboxyl, alkoxycarbonyl, and halo, or $R_1$ and $R_2$, together with the carbons to which they are bound, can be joined to form a 4 to 7 membered ring or a substituted 4 to 7 membered ring; $R_2$ is selected from the group consisting of: H, aryl, substituted aryl, alkyl, substituted alkyl, carboxyl, aminocarbonyl, alkylsulfonylaminocarboxyl, alkoxycarbonyl, and halo, or $R_2$ and $R_1$, together with the carbons to which they are bound, can be joined to form a 4 to 7 membered ring or a substituted 4 to 7 membered ring, or $R_2$ and $R_3$, together with the carbons to which they are bound, can be joined to form a 4 to 7 membered ring or a substituted 4 to 7 membered ring; $R_3$ is selected from the group consisting of: H, aryl, substituted aryl, alkyl, substituted alkyl, carboxyl, aminocarbonyl, alkylsulfonylaminocarboxyl, alkoxycarbonyl, and halo, or $R_3$ and $R_2$, together with the carbons to which they are bound, can be joined to form a 4 to 7 membered ring or a substituted 4 to 7 membered ring, or $R_3$ and $R_4$, together with the carbons to which they are bound, can be joined to form a 4 to 7 membered ring or a substituted 4 to 7 membered ring; $R_4$ is selected from the group consisting of: H, aryl, substituted aryl, alkyl, substituted alkyl, carboxyl, aminocarbonyl, alkylsulfonylaminocarboxyl, alkoxycarbonyl, and halo, or $R_4$ and $R_3$, together with the carbons to which they are bound, can be joined to form a 4 to 7 membered ring or a substituted 4 to 7 membered ring. In yet another embodiment, the coumarin fluorescent amino acid comprises a general structure III:

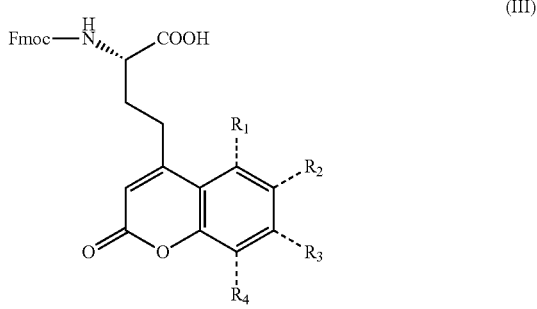

(III)

wherein $R_1$ is selected from the group consisting of: H, aryl, substituted aryl, alkyl, substituted alkyl, carboxyl, aminocarbonyl, alkylsulfonylaminocarboxyl, alkoxycarbonyl, and halo, or $R_1$ and $R_2$, together with the carbons to which they are bound, can be joined to form a 4 to 7 membered ring or a substituted 4 to 7 membered ring; $R_2$ is selected from the group consisting of: H, aryl, substituted aryl, alkyl, substituted alkyl, carboxyl, aminocarbonyl, alkylsulfonylaminocarboxyl, alkoxycarbonyl, and halo, or $R_2$ and $R_1$, together with the carbons to which they are bound, can be joined to form a 4 to 7 membered ring or a substituted 4 to 7 membered ring, or $R_2$ and $R_3$, together with the carbons to which they are bound, can be joined to form a 4 to 7 membered ring or a substituted 4 to 7 membered ring; $R_3$ is selected from the group consisting of: H, aryl, substituted aryl, alkyl, substituted alkyl, carboxyl, aminocarbonyl, alkylsulfonylaminocarboxyl, alkoxycarbonyl, and halo, or $R_3$ and $R_2$, together with the carbons to which they are bound, can be joined to form a 4 to 7 membered ring or a substituted 4 to 7 membered ring, or $R_3$ and $R_4$, together with the carbons to which they are bound, can be joined to form a 4 to 7 membered ring or a substituted 4 to 7 membered ring; $R_4$ is selected from the group consisting of: H, aryl, substituted aryl, alkyl, substituted alkyl, carboxyl, aminocarbonyl, alkylsulfonylaminocarboxyl, alkoxycarbonyl, and halo, or $R_4$ and $R_3$, together with the carbons to which they are bound, can be joined to form a 4 to 7 membered ring or a substituted 4 to 7 membered ring. In a specific embodiment, the peptide comprises a coumarin fluorescent amino acid comprising the structure IV:

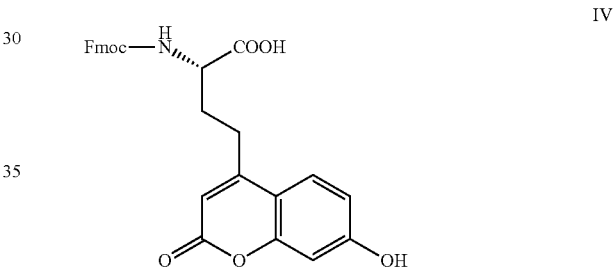

IV and a quenching fluorescent amino acid comprising the general structure V:

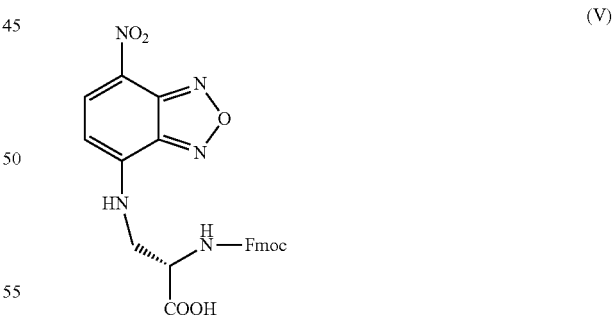

(V)

In yet another embodiment, the polypeptide comprises a sequence containing a structure selected from I or V within about 1-15 (e.g., 1-10 nm, 2-8 nm etc.) of a fluorescent amino acid selected from the group consisting of II, III, or IV. In yet another embodiment, the fluorescent coumarin amino acid and quencher amino acid are space about 2, 3, 4, 5, 6, 7, 8, 9, or 10 amino acids from each other.

It will also be recognized that the fluorophore pairs of the disclosure are useful not just in peptide, polypeptide and protein assays, but can also be used in other biological molecules such as lipids, nucleic acids and the like, where intra- or inter molecule interactions occurs. Also, the fluorophores can be used in combination with solid substrates including beads, nanoparticles, slides, tissue culture systems and the like.

Alkyl groups include straight-chain, branched and cyclic alkyl groups. Alkyl groups include those having from 1 to 20 carbon atoms. Alkyl groups include small alkyl groups having 1 to 3 carbon atoms. Alkyl groups include medium length alkyl groups having from 4-10 carbon atoms. Alkyl groups include long alkyl groups having more than 10 carbon atoms, particularly those having 10-20 carbon atoms. Cyclic alkyl groups include those having one or more rings. Cyclic alkyl groups include those having a 3-, 4-, 5-, 6-, 7-, 8-, 9- or 10-member carbon ring and particularly those having a 3-, 4-, 5-, 6-, or 7-member ring. The carbon rings in cyclic alkyl groups can also carry alkyl groups. Cyclic alkyl groups can include bicyclic and tricyclic alkyl groups. Alkyl groups optionally include substituted alkyl groups. Substituted alkyl groups include among others those which are substituted with aryl groups, which in turn can be optionally substituted. Specific alkyl groups include methyl, ethyl, n-propyl, iso-propyl, cyclopropyl, n-butyl, s-butyl, t-butyl, cyclobutyl, n-pentyl, branched-pentyl, cyclopentyl, n-hexyl, branched hexyl, and cyclohexyl groups, all of which are optionally substituted. The term cyclopentyl ring refers to a ring of five carbons with any degree of unsaturation. The term cyclohexyl ring refers to a ring of six carbons with any degree of unsaturation.

Alkenyl groups include straight-chain, branched and cyclic alkenyl groups. Alkenyl groups include those having 1, 2 or more double bonds and those in which two or more of the double bonds are conjugated double bonds. Alkenyl groups include those having from 2 to 20 carbon atoms. Alkenyl groups include small alkyl groups having 2 to 3 carbon atoms. Alkenyl groups include medium length alkenyl groups having from 4-10 carbon atoms. Alkenyl groups include long alkenyl groups having more than 10 carbon atoms, particularly those having 10-20 carbon atoms. Cyclic alkenyl groups include those having one or more rings. Cyclic alkenyl groups include those in which a double bond is in the ring or in an alkenyl group attached to a ring. Cyclic alkenyl groups include those having a 3-, 4-, 5-, 6-, 7-, 8-, 9- or 10-member carbon ring and particularly those having a 3-, 4-, 5-, 6- or 7-member ring. The carbon rings in cyclic alkenyl groups can also carry alkyl groups. Cyclic alkenyl groups can include bicyclic and tricyclic alkyl groups. Alkenyl groups are optionally substituted. Substituted alkenyl groups include among others those which are substituted with alkyl or aryl groups, which groups in turn can be optionally substituted. Specific alkenyl groups include ethenyl, prop-1-enyl, prop-2-enyl, cycloprop-1-enyl, but-1-enyl, but-2-enyl, cyclobut-1-enyl, cyclobut-2-enyl, pent-1-enyl, pent-2-enyl, branched pentenyl, cyclopent-1-enyl, hex-1-enyl, branched hexenyl, cyclohexenyl, all of which are optionally substituted.

Aryl groups include groups having one or more 5- or 6-member aromatic or heteroaromatic rings. Aryl groups can contain one or more fused aromatic rings. Heteroaromatic rings can include one or more N, O, or S atoms in the ring. Heteroaromatic rings can include those with one, two or three N, those with one or two O, and those with one or two S. Aryl groups are optionally substituted. Substituted aryl groups include among others those which are substituted with alkyl or alkenyl groups, which groups in turn can be optionally substituted. Specific aryl groups include phenyl groups, biphenyl groups, pyridinyl groups, and naphthyl groups, all of which are optionally substituted.

Arylalkyl groups are alkyl groups substituted with one or more aryl groups wherein the alkyl groups optionally carry additional substituents and the aryl groups are optionally substituted. Specific alkylaryl groups are phenyl-substituted alkyl groups, e.g., phenylmethyl groups.

Alkylaryl groups are aryl groups substituted with one or more alkyl groups wherein the alkyl groups optionally carry additional substituents and the aryl groups are optionally substituted. Specific alkylaryl groups are alkyl-substituted phenyl groups such as methylphenyl.

The rings that may be formed from two or more of R1-R4 together can be optionally substituted cycloalkyl groups, optionally substituted cycloalkenyl groups or aromatic groups. The rings may contain 3, 4, 5, 6, 7 or more carbons. The rings may be heteroaromatic in which one, two or three carbons in the aromatic ring are replaced with N, O or S. The rings may be heteroalkyl or heteroalkenyl, in which one or more $CH_2$ groups in the ring are replaced with O, N, NH, or S.

Optional substitution of any alkyl, alkenyl and aryl groups includes substitution with one or more of the following substituents: halogens, —CN, —COOR, —OR, —COR, —OCOOR, —CON(R)$_2$, —OCON(R)$_2$, —N(R)$_2$, —NO$_2$, —SR, —SO$_2$R, —SO$_2$N(R)$_2$ or —SOR groups. Optional substitution of alkyl groups includes substitution with one or more alkenyl groups, aryl groups or both, wherein the alkenyl groups or aryl groups are optionally substituted. Optional substitution of alkenyl groups includes substitution with one or more alkyl groups, aryl groups, or both, wherein the alkyl groups or aryl groups are optionally substituted. Optional substitution of aryl groups includes substitution of the aryl ring with one or more alkyl groups, alkenyl groups, or both, wherein the alkyl groups or alkenyl groups are optionally substituted.

Optional substituents for alkyl, alkenyl and aryl groups include among others:

—COOR where R is a hydrogen or an alkyl group or an aryl group and more specifically where R is methyl, ethyl, propyl, butyl, or phenyl groups all of which are optionally substituted;

—COR where R is a hydrogen, or an alkyl group or an aryl groups and more specifically where R is methyl, ethyl, propyl, butyl, or phenyl groups all of which groups are optionally substituted;

—CON(R)$_2$ where each R, independently of each other R, is a hydrogen or an alkyl group or an aryl group and more specifically where R is methyl, ethyl, propyl, butyl, or phenyl groups all of which groups are optionally substituted; R and R can form a ring which may contain one or more double bonds;

—OCON(R)$_2$ where each R, independently of each other R, is a hydrogen or an alkyl group or an aryl group and more specifically where R is methyl, ethyl, propyl, butyl, or phenyl groups all of which groups are optionally substituted; R and R can form a ring which may contain one or more double bonds;

—N(R)$_2$ where each R, independently of each other R, is a hydrogen, or an alkyl group, acyl group or an aryl group and more specifically where R is methyl, ethyl, propyl, butyl, or phenyl or acetyl groups all of which are optionally substituted; or R and R can form a ring which may contain one or more double bonds.

—SR, —SO$_2$R, or —SOR where R is an alkyl group or an aryl groups and more specifically where R is methyl, ethyl, propyl, butyl, phenyl groups all of which are optionally substituted; for —SR, R can be hydrogen;

—OCOOR where R is an alkyl group or an aryl groups;

—SO$_2$N(R)$_2$ where R is a hydrogen, an alkyl group, or an aryl group and R and R can form a ring;

—OR where R=H, alkyl, aryl, or acyl; for example, R can be an acyl yielding —OCOR* where R* is a hydrogen or an alkyl group or an aryl group and more specifically where R* is methyl, ethyl, propyl, butyl, or phenyl groups all of which groups are optionally substituted.

Specific substituted alkyl groups include haloalkyl groups, particularly trihalomethyl groups and specifically trifluoromethyl groups. Specific substituted aryl groups include mono-, di-, tri, tetra- and pentahalo-substituted phenyl groups; mono-, di-, tri-, tetra-, penta-, hexa-, and hepta-halo-substituted naphthalene groups; 3- or 4-halo-substituted phenyl groups, 3- or 4-alkyl-substituted phenyl groups, 3- or 4-alkoxy-substituted phenyl groups, 3- or 4-RCO-substituted phenyl, 5- or 6-halo-substituted naphthalene groups. More specifically, substituted aryl groups include acetylphenyl groups, particularly 4-acetylphenyl groups; fluorophenyl groups, particularly 3-fluorophenyl and 4-fluorophenyl groups; chlorophenyl groups, particularly 3-chlorophenyl and 4-chlorophenyl groups; methylphenyl groups, particularly 4-methylphenyl groups, and methoxyphenyl groups, particularly 4-methoxyphenyl groups.

A polypeptide or peptide comprising a FRET pair of fluorescent amino acids is provided. In one embodiment, the peptide or polypeptide may be a ligand or a substrate. For example, the substrate may be a protease substrate or other enzymatic substrate (e.g., a ligase substrate). In certain embodiment, the substrate may comprise one or more FRET pairs at different locations so long as the pairs are in a proximity to undergo FRET (e.g., about 1 to about 10 nm-1, 2, 3, 4, 5, 6, 7, 8, 9, 10, 11, 12, 13, 14, or 15 nm). In a specific embodiment the pair comprise a coumarin fluorescent amino acid and an NBD amino acid or derivative thereof.

A polypeptide or peptide comprising a FRET pair of fluorescent amino acids as described herein may be operably linked or fused to an additional peptide or polypeptide. For example, cell penetrating peptides (CPPs) can be used to promote uptake of a synthesized peptide of the disclosure.

A CPP comprises an amino acid sequences having a strong alpha helical structure with arginine (Arg) residues down the helical cylinder. In yet another embodiment, the CPP domain comprises a peptide represented by the following general formula: $B_1$-$X_1$-$X_2$-$X_3$-$B_2$-$X_4$-$X_5$-$B_3$ (SEQ ID NO:2) wherein $B_1$, $B_2$, and $B_3$ are each independently a basic amino acid, the same or different; and $X_1$, $X_2$, $X_3$, $X_4$ and $X_5$ are each independently an alpha-helix enhancing amino acid, the same or different. In another embodiment, the CPP domain is represented by the following general formula: $B_1$-$X_1$-$X_2$-$B_2$-$B_3$-$X_3$-$X_4$-$B_4$ (SEQ ID NO:3) wherein $B_1$, $B_2$, $B_3$, and $B_4$ are each independently a basic amino acid, the same or different; and $X_1$, $X_2$, $X_3$, and $X_4$ are each independently an alpha-helix enhancing amino acid the same or different.

Additionally CPP domains comprise basic residues, e.g., lysine (Lys) or arginine (Arg), and further including at least one proline (Pro) residue sufficient to introduce "kinks" into the domain. Examples of such domains include the transduction domains of prions. For example, such a peptide comprises KKRPKPG (SEQ ID NO:4).

In one embodiment, the domain is a peptide represented by the following sequence: X-X-R-X-(P/X)-(B/X)-B-(P/X)-X-B-(B/X) (SEQ ID NO:5), wherein X is any alpha helical promoting residue such as alanine; P/X is either proline or X as previously defined; B is a basic amino acid residue, e.g., arginine (Arg) or lysine (Lys); R is arginine (Arg) and B/X is either B or X as defined above.

In another embodiment the CPP is cationic and consists of between 7 and 10 amino acids and has the formula K-$X_1$-R-$X_2$-$X_1$ (SEQ ID NO:6) wherein $X_1$ is R or K and $X_2$ is any amino acid. An example of such a peptide comprises RKKRRQRRR (SEQ ID NO:7).

Additional transducing domains include a TAT fragment that comprises at least amino acids 49 to 56 of TAT up to about the full-length TAT sequence. A TAT fragment may include one or more amino acid changes sufficient to increase the alpha-helicity of the fragment. In some instances, the amino acid changes introduced will involve adding a recognized alpha-helix enhancing amino acid. Alternatively, the amino acid changes will involve removing one or more amino acids from the TAT fragment that impede alpha helix formation or stability. In a more specific embodiment, the TAT fragment will include at least one amino acid substitution with an alpha-helix enhancing amino acid. Typically a TAT fragment or other CPPs will be made by standard peptide synthesis techniques although recombinant DNA approaches may be used in some cases.

Fluorescent amino acids can be incorporated into a peptide or polypeptide using chemical synthesis techniques or through expression in an appropriate system that allows for incorporation of the amino acid using tRNA's capable of utilizing such unnatural amino acids.

Polypeptide comprising fluorescent amino acids can be synthesized by commonly used methods such as those that include t-BOC or FMOC protection of alpha-amino groups. Both methods involve stepwise synthesis in which a single amino acid is added at each step starting from the C terminus of the peptide (See, Coligan, et al., Current Protocols in Immunology, Wiley Interscience, 1991, Unit 9). Such polypeptides can also be synthesized by the well known solid phase peptide synthesis methods such as those described by Merrifield, J. Am. Chem. Soc., 85:2149, 1962; and Stewart and Young, Solid Phase Peptides Synthesis, Freeman, San Francisco, 1969, pp. 27-62, using a copoly(styrene-divinylbenzene) containing 0.1-1.0 mmol amines/g polymer. On completion of chemical synthesis, the peptide or polypeptide can be deprotected and cleaved from the polymer by treatment with liquid HF-10% anisole for about ¼-1 hours at 0° C. After evaporation of the reagents, the peptides are extracted from the polymer with a 1% acetic acid solution, which is then lyophilized to yield the crude material. The peptide or polypeptide can be purified by such techniques as gel filtration on Sephadex G-15 using 5% acetic acid as a solvent. Lyophilization of appropriate fractions of the column eluate yield homogeneous peptide or polypeptide, which can then be characterized by standard techniques such as amino acid analysis, thin layer chromatography, high performance liquid chromatography, ultraviolet absorption spectroscopy, molar rotation, or measuring solubility.

Biosynthetic methods that employ chemically modified aminoacyl-tRNAs have been used to incorporate several biophysical probes into proteins (e.g., Brunner, J. New Photolabeling and crosslinking methods, Annu. Rev Biochem, 483-514 (1993); and, Krieg, U. C., Walter, P., Hohnson, A. E. Photocrosslinking of the signal sequence of nascent preprolactin of the 54-kilodalton polypeptide of the signal recognition particle, Proc. Natl. Acad. Sci, 8604-8608 (1986)).

It has been shown that fluorescent amino acids can be site-specifically incorporated into proteins in vitro by the addition of chemically aminoacylated suppressor tRNAs to protein synthesis reactions programmed with a gene containing a desired amber nonsense mutation. Using these approaches, one can substitute a number of the common twenty amino acids with close structural homologues, e.g., fluorophenylalanine for phenylalanine, using strains auxotrophic for a particular amino acid. See, e.g., Noren, C. J., Anthony-Cahill, Griffith, M. C., Schultz, P. G. A general method for site-specific incorporation of fluorescent amino acids into proteins, Science, 244: 182-188 (1989); M. W. Nowak, et al., Science 268:439-42 (1995); Bain, J. D., Glabe, C. G., Dix, T. A., Chamberlin, A. R., Diala, E. S. Biosynthetic site-specific Incorporation of a non-natural amino acid into a polypeptide, J. Am Chem Soc, 111:8013-8014 (1989); N. Budisa et al., FASEB J. 13:41-51 (1999); Ellman, J. A., Mendel, D., Anthony-Cahill, S., Noren, C. J., Schultz, P. G. Biosynthetic method for introducing fluorescent amino acids site-specifically into proteins, Methods in Enz., 301-336 (1992); and, Mendel, D., Cornish, V. W. & Schultz, P. G. Site-Directed Mutagenesis with an Expanded Genetic Code, Annu Rev Biophys. Biomol Struct. 24, 435-62 (1995); Isabelle Dufau, Honore Mazarguil, Design of a fluorescent amino acid derivative usable in peptide synthesis Tetrahedron Letters, 41:6063-6066, 2000).

For example, a suppressor tRNA can be prepared to recognize the stop codon UAG and was chemically aminoacylated with a fluorescent amino acid. Conventional site-directed mutagenesis can be used to introduce the stop codon TAG, at the site of interest in a coding sequence. See, e.g., Sayers, J. R., Schmidt, W. Eckstein, F. 5', 3'Exonuclease in phosphorothioate-based oligonucleotide-directed mutagenesis, Nucleic Acids Res, 791-802 (1988). When the acylated suppressor tRNA and the mutant gene are combined in an in vitro transcription/translation system, the fluorescent amino acid is incorporated in response to the UAG codon which results in a protein containing that amino acid at the specified position.

Microinjection techniques can also be used to incorporate fluorescent amino acids into proteins. See, e.g., Nowak et al., Science, 268:439 (1995) and D. A. Dougherty, Curr. Opin. Chem. Biol., 4:645 (2000). For example, a cell can be injected with an mRNA encoding a target protein with a UAG stop codon at the amino acid position of interest and an amber suppressor tRNA aminoacylated with the desired fluorescent amino acid. The translational machinery of the cell then inserts the fluorescent amino acid at the position specified by the UAG codon. Examples include the incorporation of a fluorescent amino acid into tachykinin neurokinin-2 receptor to measure distances by fluorescence resonance energy transfer, see, e.g., G. Turcatti, K. Nemeth, M. D. Edgerton, U. Meseth, F. Talabot, M. Peitsch, J. Knowles, H. Vogel and A. Chollet, J. Biol. Chem., 271:19991 (1996); the incorporation of biotinylated amino acids to identify surface-exposed residues in ion channels, see, e.g., J. P. Gallivan, H. A. Lester and D. A. Dougherty, Chem. Biol., 4:739 (1997); the use of caged tyrosine analogs to monitor conformational changes in an ion channel in real time, see, e.g., J. C. Miller, S. K. Silverman, P. M. England, D. A. Dougherty and H. A. Lester, Neuron, 20:619 (1998); and, the use of alpha hydroxy amino acids to change ion channel backbones for probing their gating mechanisms. See, e.g., P. M. England, Y. Zhang, D. A. Dougherty and H. A. Lester, Cell, 96:89 (1999); and, T. Lu, A. Y. Ting, J. Mainland, L. Y. Jan, P. G. Schultz and J. Yang, Nat. Neurosci., 4:239 (2001).

The ability to include fluorescent amino acids with various sizes, acidities, nucleophilicities, hydrophobicities, and other properties into proteins can greatly expand the ability to rationally and systematically manipulate the structures of proteins and probe protein function.

The disclosure contemplates the use of polypeptide comprising fluorescent amino acids and a combination of both natural and fluorescent amino acids. Techniques for the incorporation of fluorescent amino acid in vivo have been developed. For example, an organism or system comprising an orthogonal tRNA (O-tRNA) and an orthogonal aminoacyl tRNA synthetase (O-RS) can be used. Typically, the O-RS preferentially aminoacylates the O-tRNA with at least one fluorescent amino acid in the translation system and the O-tRNA recognizes at least one selector codon. The translation system thus inserts the fluorescent amino acid into a protein produced in the system, in response to an encoded selector codon.

A translation systems includes both cells, such as bacterial cells (e.g., *Escherichia coli*), archeaebacterial cells, eukaryotic cells (e.g., yeast cells, mammalian cells, plant cells, insect cells), as well as cell-free system (e.g., an in vitro translation system, such as a translation extract from a cellular extract).

Any of a codons can be used to incorporate an fluorescent amino acid including nonsense codons, rare codons, four (or more) base codons, or the like. In one embodiment, codon is an amber codon, or an opal codon, a fluorescent codon, at least a four base codon or the like. A number of codons can be introduced into a desired gene.

The 64 genetic codons code for 20 amino acids and 3 stop codons. Because only one stop codon is needed for translational termination, the other two stop codons can in principle be used to encode nonproteinogenic amino acids. The amber stop codon, UAG, has been successfully used in in vitro biosynthetic system to direct the incorporation of fluorescent amino acids. Among the 3 stop codons, UAG is the least used stop codon in *Escherichia coli*. Some *Escherichia coli* strains contain natural suppressor tRNAs, which recognize UAG and insert a natural amino acid.

Codons comprising four or more base codons can also be used in the disclosure. Examples of four base codons include, for example, UAGA, CUAG, AGGA, CCCU, and the like. Examples of five base codons include, e.g., CUAGA, CUACU, AGGAC, CCCCU, CCCUC, UAGGC, and the like. For example, in the presence of mutated O-tRNAs such as a special frameshift suppressor tRNAs, with anticodon loops the four or more base codon is read as single amino acid.

Proteins or polypeptides that can be generated are not to be limited by the disclosure. Any polypeptide capable of detection or analysis can be used. For example, the protein can be an enzymatic protein, receptor protein, receptor ligand protein, membrane protein, secondary messenger proteins, a therapeutic protein and the like. For example, the protein comprising a FRET pair of fluorescent amino acids can comprise a polypeptide selected from the group consisting of a cytokine, erythropoietin (EPO), insulin, human growth hormone, epithelial Neutrophil Activating Peptide-78, a growth factor, a growth factor receptor, an interferon, an interleukin (e.g., IL-1, an IL-2, an IL-3, an IL-4, an IL-5, an IL-6, an IL-7, an IL-8, an IL-9, an IL-10, an IL-11, an IL-12), a transcriptional activator, an inflammatory molecule, an oncogene product, a peptide hormone, a signal transduction molecule, a steroid hormone receptor, a transcriptional suppressor, GRO-α, -β, -γ, -δ, hepatocyte growth factor, insulin-like growth factor, leukemia inhibitory factor, oncostatin M, PD-ECSF, PDGF, pleiotropin, SCF, VEGEF, G-CSF, fibroblast growth factor, platelet derived growth factor, tumor necrosis factor, transforming growth faction-α, -β, epidermal growth factor, keratinocyte growth factor, stem cell factor, CD40L/CD40, VLA-4/VCAM-1, ICAM-1/LFA-1, hyalurin/CD44, Mos, Ras, Raf, Met; p53, Jun, Myb, Rel, Tat, Fos, Myc, testosterone receptor, estrogen receptor, progesterone receptor, aldosterone receptor, LDL receptor, corticosterone, alpha-1 antitrypsin, angiostatin, an apolipoprotein, an apoprotein, a chemokine, collagen, factor IX, factor VII, factor VIII, factor X, G-CSF, GM-CSF, serum albumin, somatostatin, to name but a few.

A polypeptide comprising a FRET pair of fluorescent amino acids can contain any number of fluorescent amino acids (e.g., from 1-15 or more). For example, the protein can comprise 1, 2, 3, 4, 5, 6, 7, 6, 9, 10, 11, 12, 13, 14, 15 or more fluorescent amino acids. The fluorescent amino acids can be the same or different. In one embodiment, the protein comprises at least two fluorescent amino acids capable of undergoing FRET. In a specific embodiment, the at least to fluorescent amino acids capable of undergoing FRET comprises an NBD or derivative thereof or a CUM or derivative thereof. In another embodiment, the FRET pair can comprise a G5 and G6 fluorescent amino acid.

A translation system can be used to produce a polypeptide comprising at least one fluorescent amino acid by providing polynucleotide comprising at least one codon recognized by a tRNA fluorescent amino acid, wherein the polynucleotide encodes a protein of interest. The translation system comprises an orthogonal tRNA (O-tRNA) that functions in the translation system and recognizes the codon and an orthogonal aminoacyl tRNA synthetase (O-RS), that aminoacylates the O-tRNA with a fluorescent amino acid in the translation system. The translation system further comprises a fluorescent amino acid. Using the methods described herein a protein comprising a fluorescent amino acids can be produced that can be stably folded, glycosylated, or otherwise modified.

The disclosure provides methods, kits and compositions useful for analyzing protein structure, function and structure-function relationships. In addition, the disclosure provides methods useful for identifying binding ligands and substrates for protein or enzyme. The methods, kits and compositions of the disclosure utilize, in one embodiment, fluorescent amino acids that are capable of acting as an acceptor or donor of electromagnetic radiation (e.g., Förster resonance energy transfer (FRET)). Using the incorporation of such fluorescent amino acids FRET techniques can be used to measure the relationship between amino acids within a single polypeptide (e.g., to determine distance between amino acids in an active site), to measure putative ligand binding, wherein a polypeptide comprises one fluorescent amino acid in a binding site and the ligand comprises a different FRET moiety (or vice versa), or a polypeptide having enzymatic activity with an fluorescent amino acid in the active site or co-factor site and a FRET moiety within the substrate (or vice versa).

In one embodiment, a method of identifying a binding ligand or substrate for a target polypeptide comprises providing a polynucleotide comprising at least one codon that results in the incorporation of at least one fluorescent amino acid upon translation, wherein the fluorescent amino acid comprises a first acceptor or donor chromophore moiety; translating the polynucleotide to obtain a fluorescent polypeptide comprising the at least one fluorescent amino acid; contacting fluorescent polypeptide with a putative binding ligand comprising a second acceptor or donor chromophore moiety, wherein the first and second acceptor or donor chromophore moieties are different, wherein the first and second acceptor or donor chromophore moieties are selected to undergo Förster resonance energy transfer (FRET) when a binding ligand is bound to a target polypeptide, and identifying FRET, wherein the presence of FRET is indicative that the putative binding ligand binds to the target polypeptide thereby identifying the binding ligand. In one embodiment, the first fluorescent amino acid is a CUM amino acid or derivative thereof and the second fluorescent amino acid in the corresponding ligand is a quenching fluorescent amino acid (e.g., an NBD or derivative thereof).

In one embodiment, a method of identifying a binding ligand or substrate for a target polypeptide comprises providing a polynucleotide comprising at least two codon that results in the incorporation of at least one fluorescent amino acid upon translation (e.g., a CUM amino acid or derivative thereof), wherein the fluorescent amino acid comprises a first fluorophore moiety; and a second codon that results in the incorporation of a second quenching fluorophore (e.g., NBD or a derivative thereof); translating the polynucleotide to obtain a polypeptide comprising the at least two fluorescent amino acid; contacting the polypeptide with a putative binding ligand or interacting protein; exciting the polypeptides with an excitation wavelength and measuring emission spectra, wherein the presence of FRET is indicative that the putative binding ligand or interacting protein binds to the target polypeptide thereby identifying the ligand or substrate.

The disclosure provides, for example, FRET-based high-throughput screening for SUMO ligase or protease inhibitors. SUMO, known as small ubiquitin-related modifier, is a family of post-translational protein modifiers involved in immune signal transduction, transcriptional regulation and neurodegenerative diseases. SUMO undergoes reversible conjugation to the target protein via the help of SUMO ligases, and this process has been proven to be required for most eukaryotic organisms. Screening of small chemical inhibitors of SUMO ligases are important because small chemicals offer better spatial and temporal control of SUMOylation process compared with traditional methods such as gene knockout studies. Incorporating fluorescent amino acid-L-(7-hydroxycoumarin-4-yl)ethylglycine (CUM) into this reporter to facilitate the high-throughput screening for SUMO ligase inhibitors promotes discovery.

SUMOylation is an important post-translational protein modification mechanism which plays an important role in a variety of biological processes. Via the catalysis of multiple enzymes, SUMO peptides are reversibly conjugated to the lysine resides of target proteins to modify their localization and functions. Conjugation and deconjugation of SUMO is a cascade event requiring multiple protein-protein interactions. SUMO peptides interact with a series of enzymes including the E1 activating enzyme, E2 conjugating enzyme and E3 ligases. These enzymes also interact with each other and the target proteins to facilitate the transfer of SUMO peptides. The nature of the SUMOylation network indicates a great potential for small chemical inhibitors to be used in the investigation and manipulation of this important process.

Using fluorescent proteins to tag protein components involved in the SUMOylation process successfully detected the interaction of SUMO with the E2 enzyme and one E3 ligase. The disclosure provides a FRET-based method to analyze the interaction between SUMO and other components involved in the SUMOylation network. The methods and compositions of the disclosure are applicable to high-throughput screening assay to look for small chemical inhibitors which can specifically disrupt protein-protein interactions involved in this network. The small chemical inhibitors will not only contribute to the investigation of SUMOylation and improve the knowledge about this important process, but the work will also provide a novel approach for high-throughput screening assays targeting protein-protein interactions.

The disclosure can use both traditional fluorophores, modified fluorophores or fluorescent amino acids that are capable of fluorescence. Large fluorescent moieties may result in spatial hindrance and interference, however, such interference can be determined empirically. In another aspect, the disclosure can use fluorescent amino acid with novel side chain groups which can be genetically encoded and incorporated into proteins with high specificity to measure protein function and structure. FRET reporter protein with fluorescent amino acids or fluorescent moieties to facilitate the high-throughput screening of, for example, SUMO ligase inhibitors, which will be important in studies of cytokine signaling pathways.

Protein post-translational modifications are general mechanisms that alter protein functions in most cells, especially in eukaryotic cells. Common modifications involve attachment of small chemical moieties such as phosphate, acetyl or methyl groups, which plays a key role in many cellular events including signaling transduction, DNA repair and transcriptional regulation. Besides those small chemical moieties, small peptides can also function as protein modifiers. Ubiquitin, a 76-residue peptide, is a well studied protein modifier whose covalent modification can result in proteasome-mediated degradation of target proteins. SUMO, known as Small Ubiquitin-related MOdifier, has emerged as an important protein modifier in recent years. Composed of ~100 amino acids, SUMO undergoes reversible conjugation to the lysine residues of target proteins (SUMOylation) via the catalysis of various enzymes. Although structurally related to ubiquitin, SUMO shares only 18% sequence identity with ubiquitin and has very different effects on target proteins. SUMOylation in a target-specific manner can affect a target protein's intracellular localization, its ability to interact with other proteins or its transcriptional activity. SUMOylation may also compete with ubiquitination on the same lysine residue to increase the stability of target proteins. Given its important role in many biological processes, SUMO is required for most eukaryotic organisms. Although not well understood yet, there have been reports linking misregulated SUMOylation to some human diseases including neurodegenerative diseases and viral infection.

Figure 17:
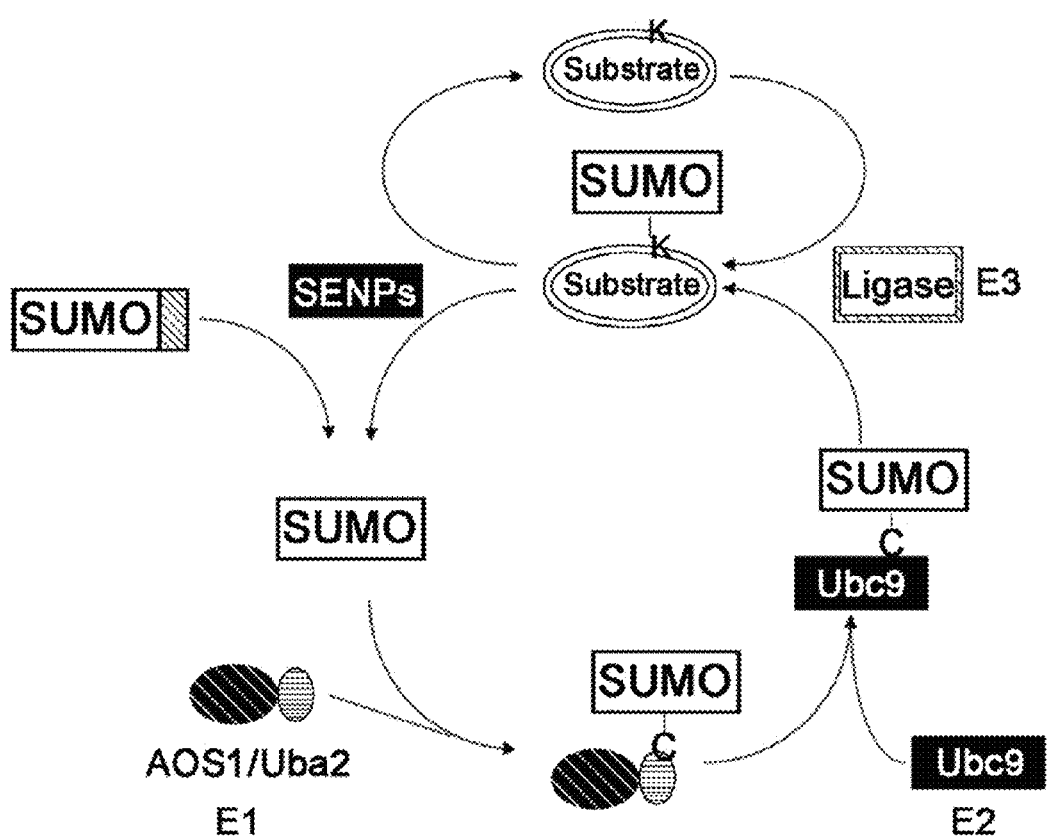
FIG. 17 depicts conjugation and deconjugation of SUMO to and from substrate proteins require multiples enzymes.

Analogous to ubiquitination, conjugation and deconjugation of SUMO require the catalysis of multiple enzymes (FIG. 17). SUMO is translated from mRNA as a precursor protein. Pre-SUMO is then recognized by SUMO-specific peptidases (SENPs) and cleaved to generate a C-terminal Gly-Gly motif. The heterodimer Aos1/Uba2, which is the SUMO E1 activating enzyme, then forms a thioester bond with SUMO using the energy from the degradation of ATP. SUMO is further transferred from the E1 enzyme to the active site cysteine of the SUMO E2 conjugating enzyme Ubc9. Catalyzed by SUMO E3 ligases, SUMO is finally transferred from Ubc9 to the lysine residue of target proteins. SUMOylated proteins can then be recognized by SENPs and free SUMO is cleaved off to be used for the conjugation to other proteins. Protein-protein interactions are crucial for SUMOylation to proceed. Using X-ray crystallography and protein-protein interaction assays such as yeast two-hybrid, interactions between different protein components have been investigated in the past few years. Cocrystallization of SUMO-E1 showed SUMO interacts with two distinct domains of heterodimer Aos1/Uba2 to form the thioester bond. Ubc9 possesses several protein interaction sites for E1, SUMO and E3 ligases and functions as the core components in the cascade. SUMO E3 ligases interact with both substrate proteins and Ubc9/SUMO to facilitate transfer of SUMO by recruitment of substrate proteins.

As a three-enzyme cascade, SUMOylation involves many enzymes with different specificities. SUMO itself represents a family of closely related proteins. Four SUMO isoforms have been identified in human named as SUMO-1 to SUMO-4. Except SUMO-4 which is only expressed in the kidney and spleen, all SUMO proteins are ubiquitously expressed at all developmental stages. While SUMO isoforms share high sequence identity with each other (50% between SUMO-1 and SUMO-2, and 95% between SUMO-2 and SUMO-3), these isoforms are not functionally identical. Conjugation of SUMO2/3 but not SUMO-1 can be induced in response of certain stresses. Different SUMO isoforms are also used preferentially to modify different substrate proteins.

Figure 4:
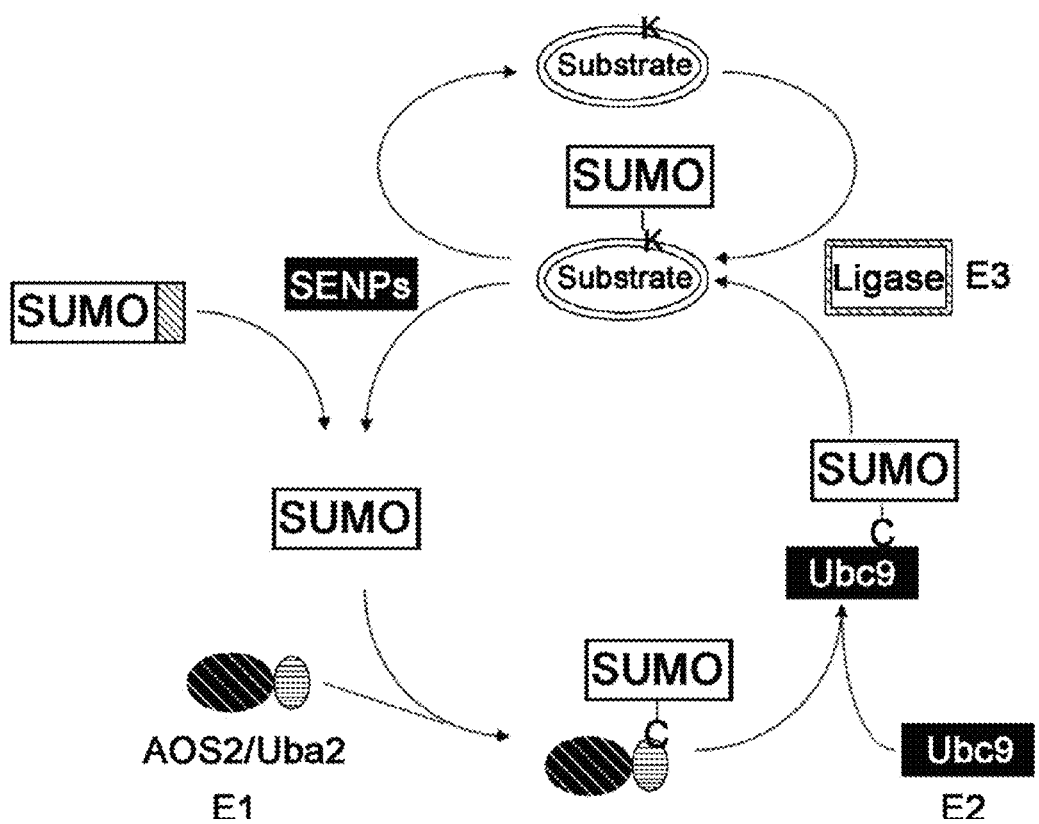
FIG. 4 shows the SUMO pathway and the SUMOylation in the JAK/STAT pathway.
Figure 4:
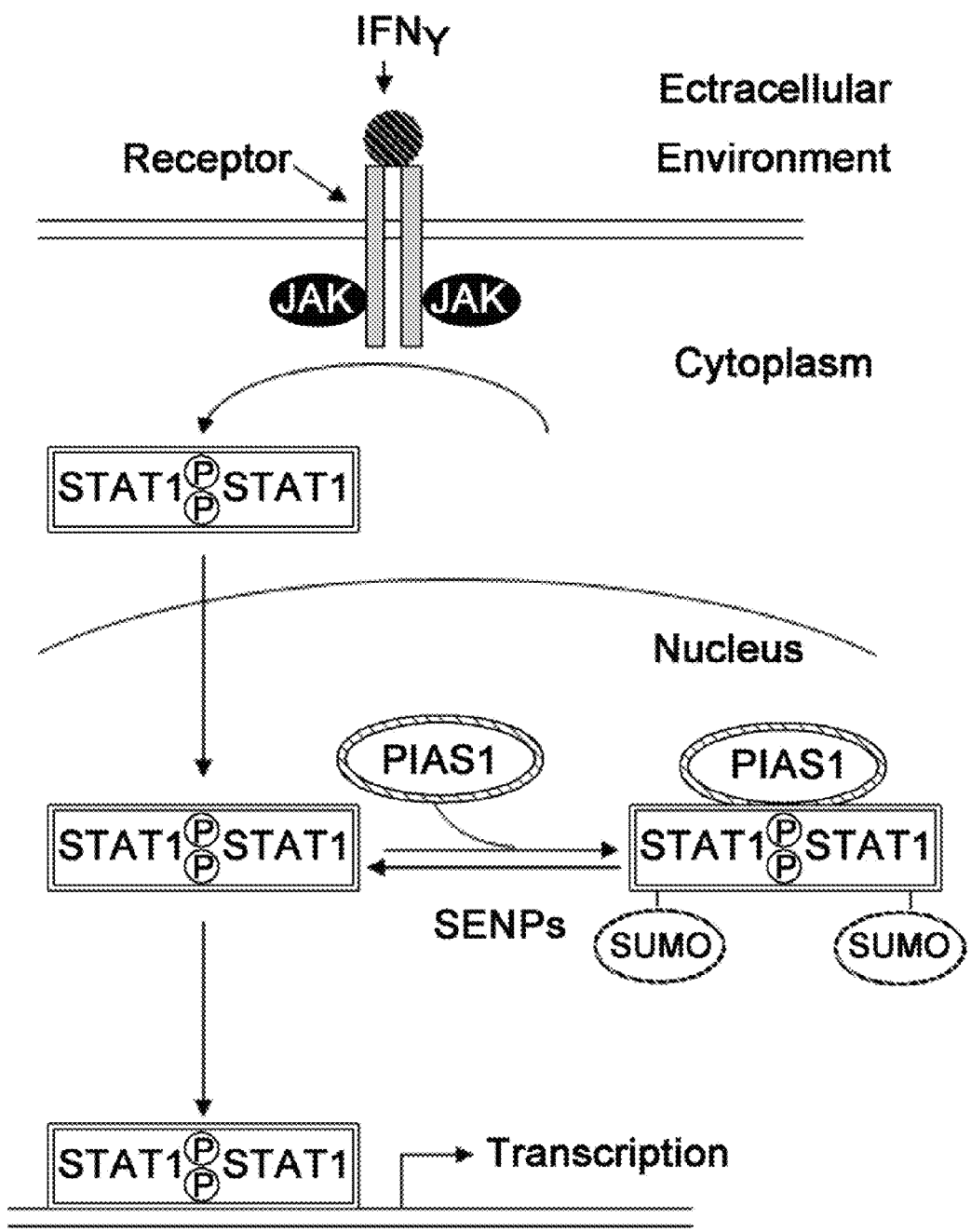
Figure 5:
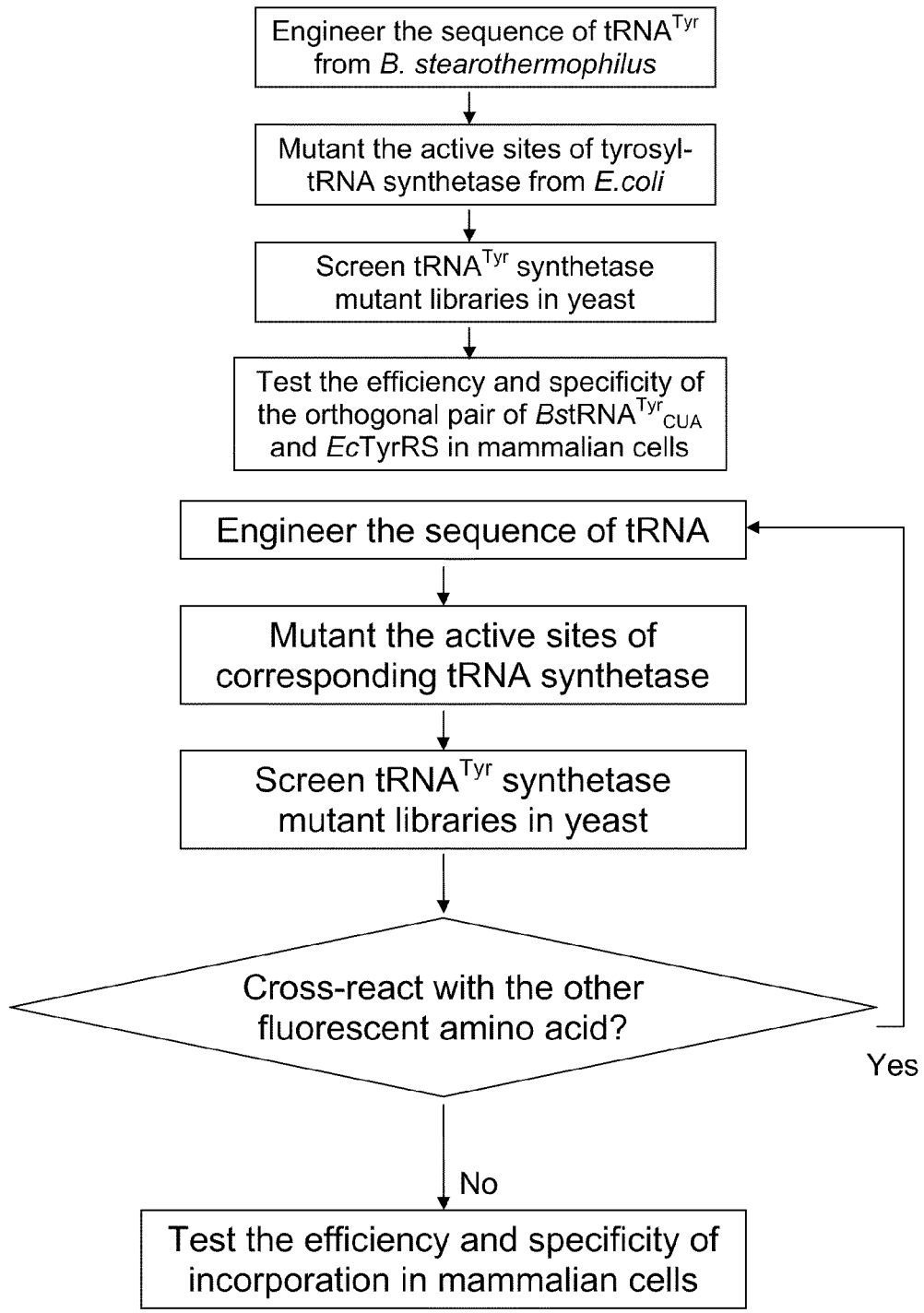
FIG. 5 shows process of development of orthogonal pair of aminoacyl-tRNA synthetase (aaRS) and amber suppressor tRNA to incorporate the fluorescent amino acid L-(7-hydroxycoumarin-4-yl)ethylglycine.
Figure 6:
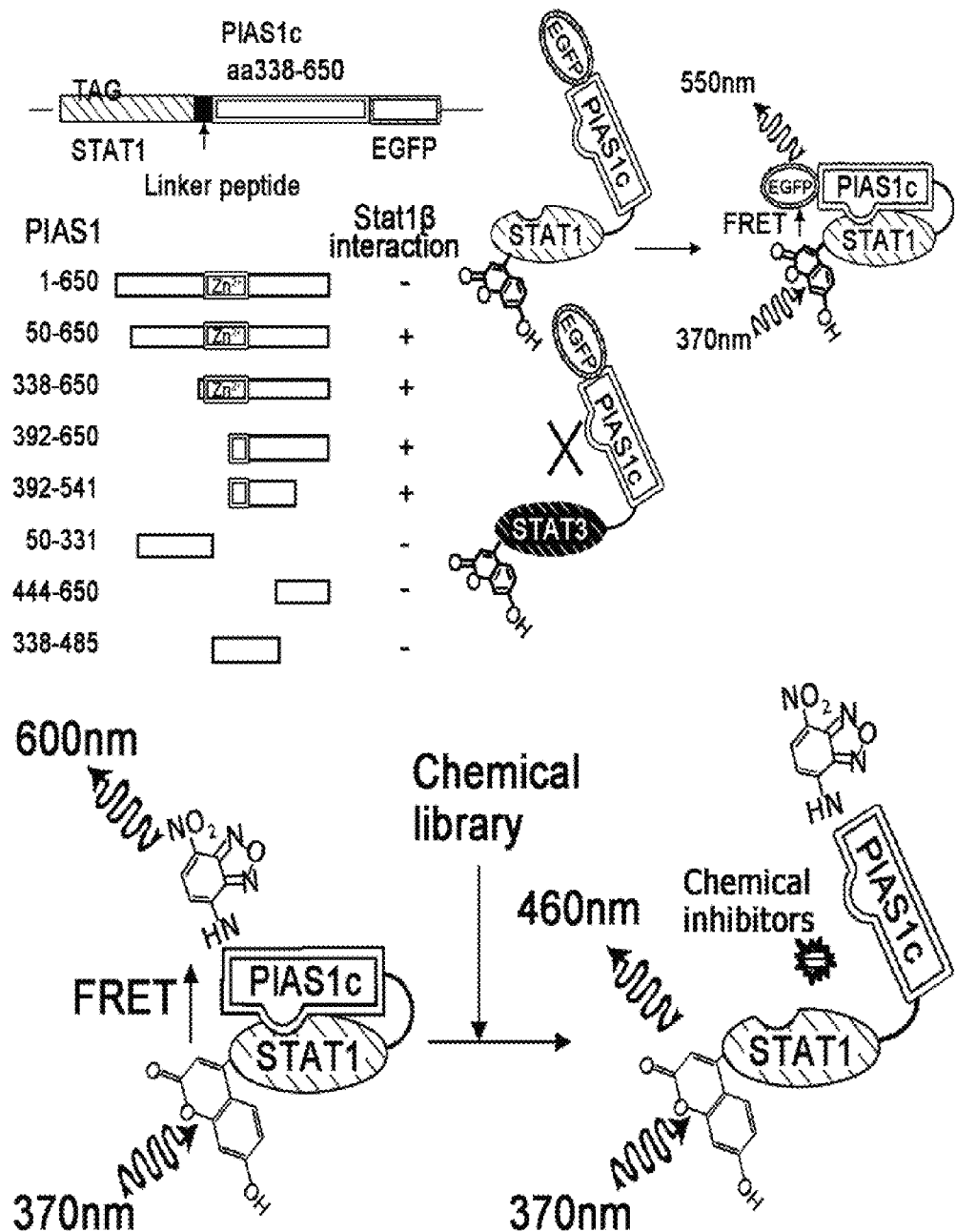
FIG. 6 depicts a concept of the disclosure. Although the SUMO pathway is depicted, any polypeptide interaction can be substituted.
Figure 7:
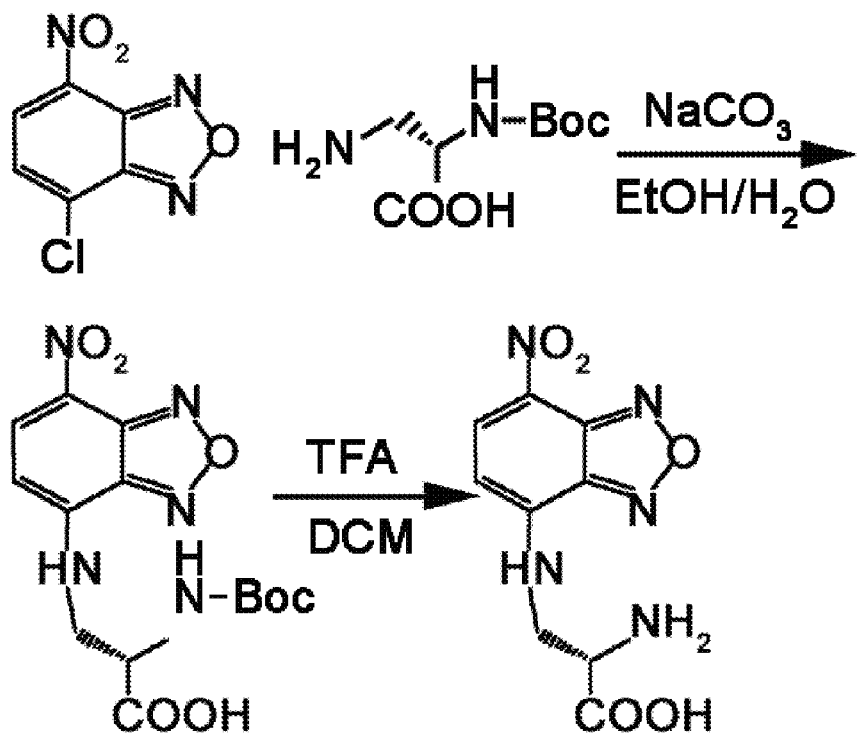
FIG. 7 shows a development of an orthogonal pair of aaRS and opal/ochre suppressor tRNA to incorporate 3-[(7-nitro-2,1,3-benzoxadiazol-4-yl)amino]-L-alanine(NBD-alanine) into proteins in mammalian cells and test the FRET efficiency of two fluorescent amino acids in the FRET reporter.
Figure 7:
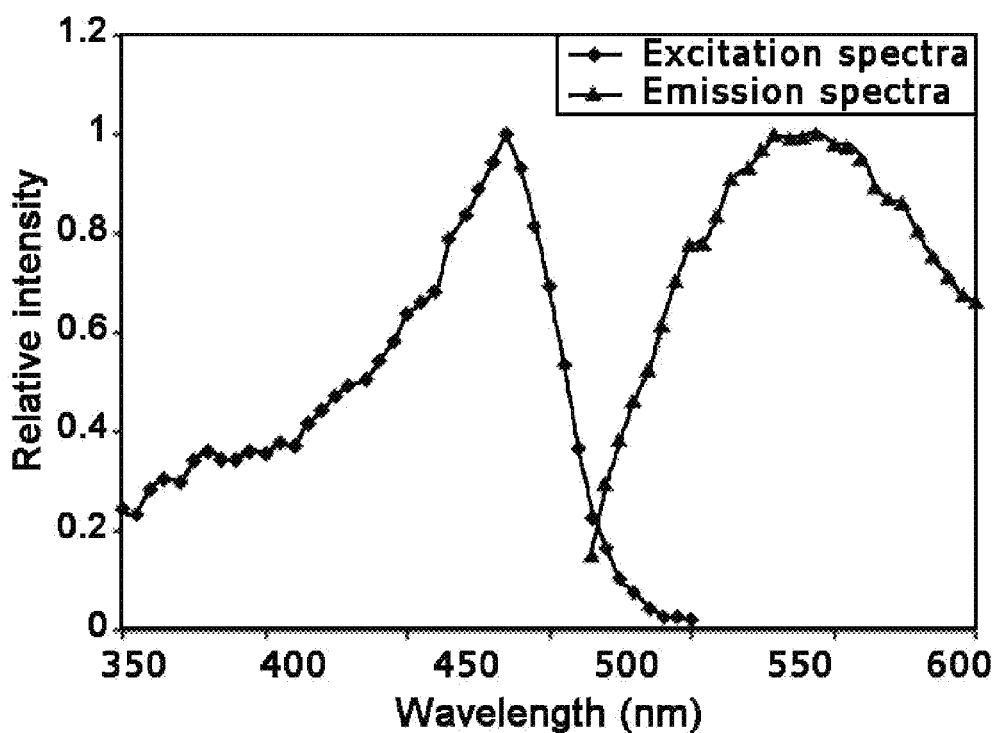
Figure 8:
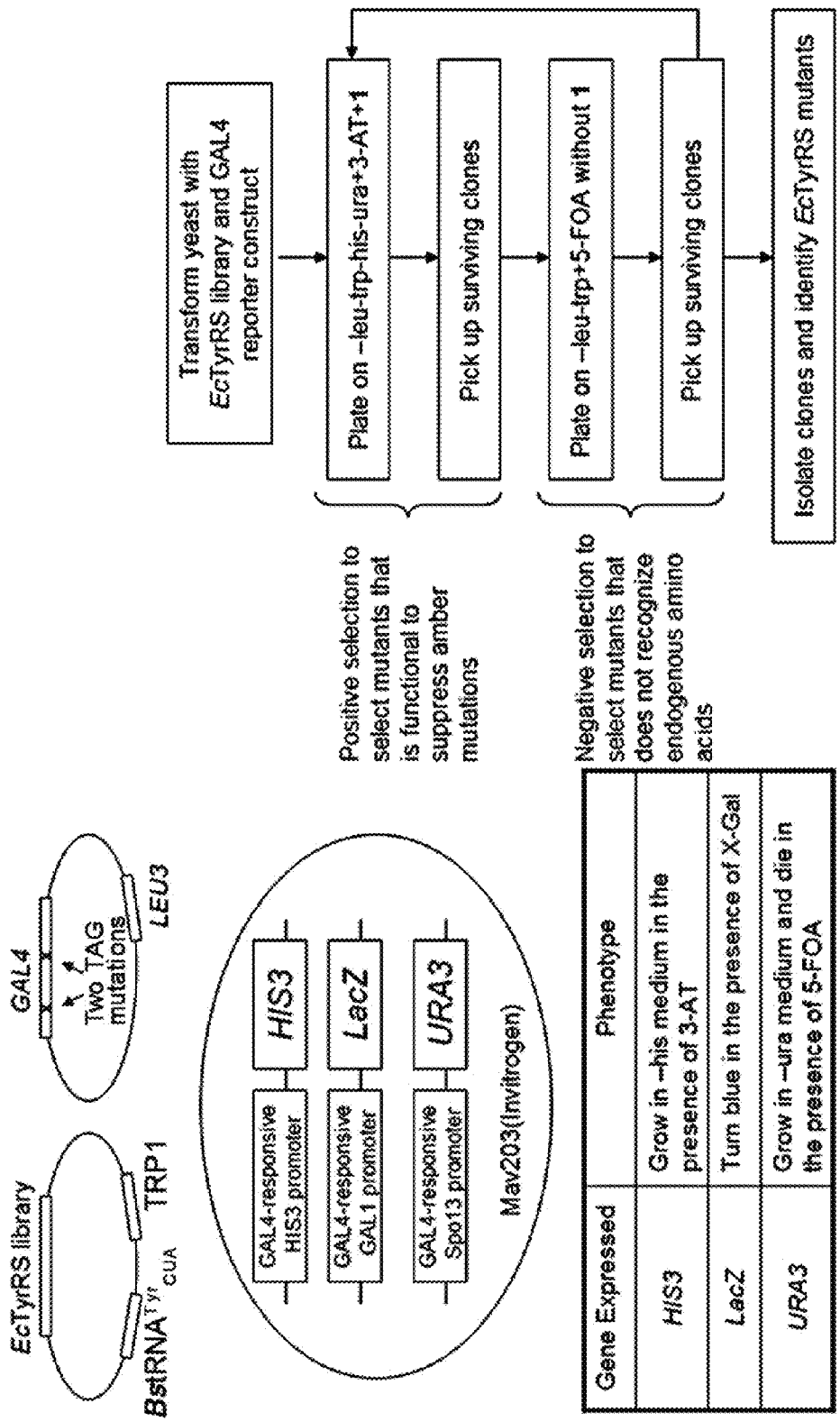
FIG. 8 shows a scheme of EcTyrRS selection in yeast.
Figure 9:
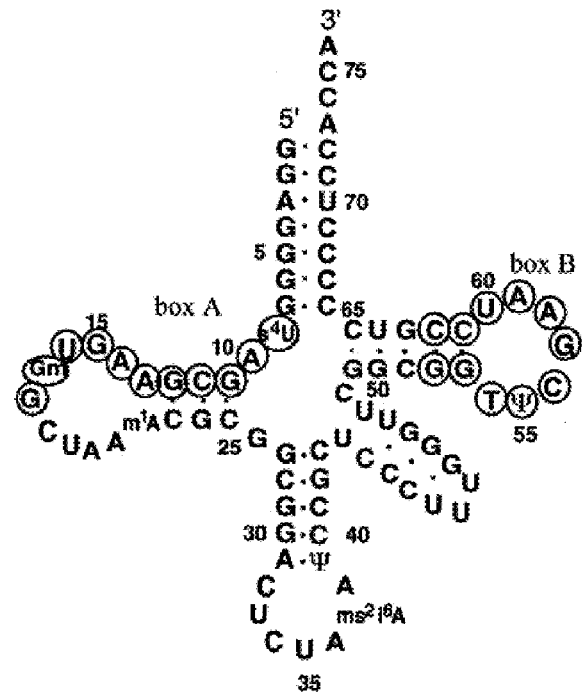
FIG. 9 shows the structure of a tRNA$^{tyr}$ (SEQ ID NO:1).
Figure 10:
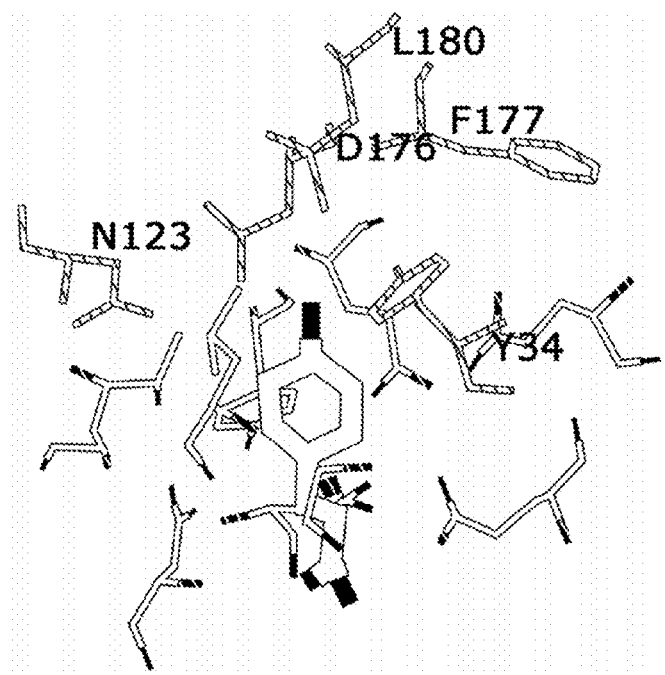
FIG. 10 shows Active site of $E.\ coli$ tyrosyl-tRNA synthetase.
Figure 11:
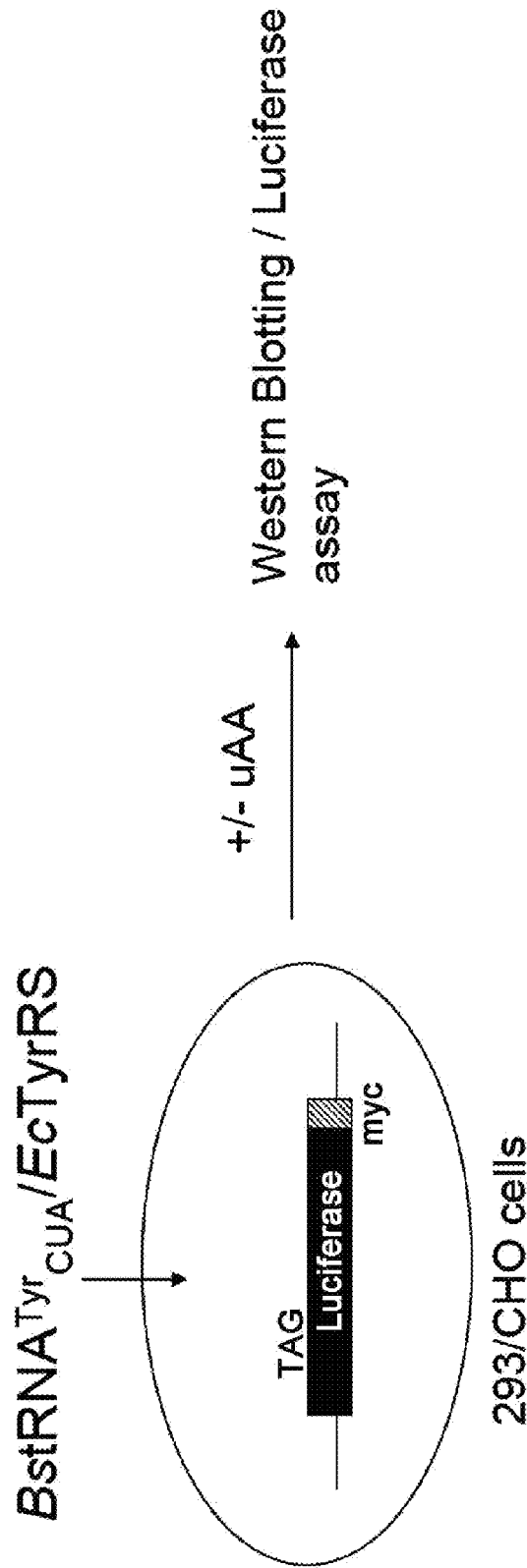
FIG. 11 shows a method of testing incorporation efficiency and specificity in mammalian cells.
Figure 12:
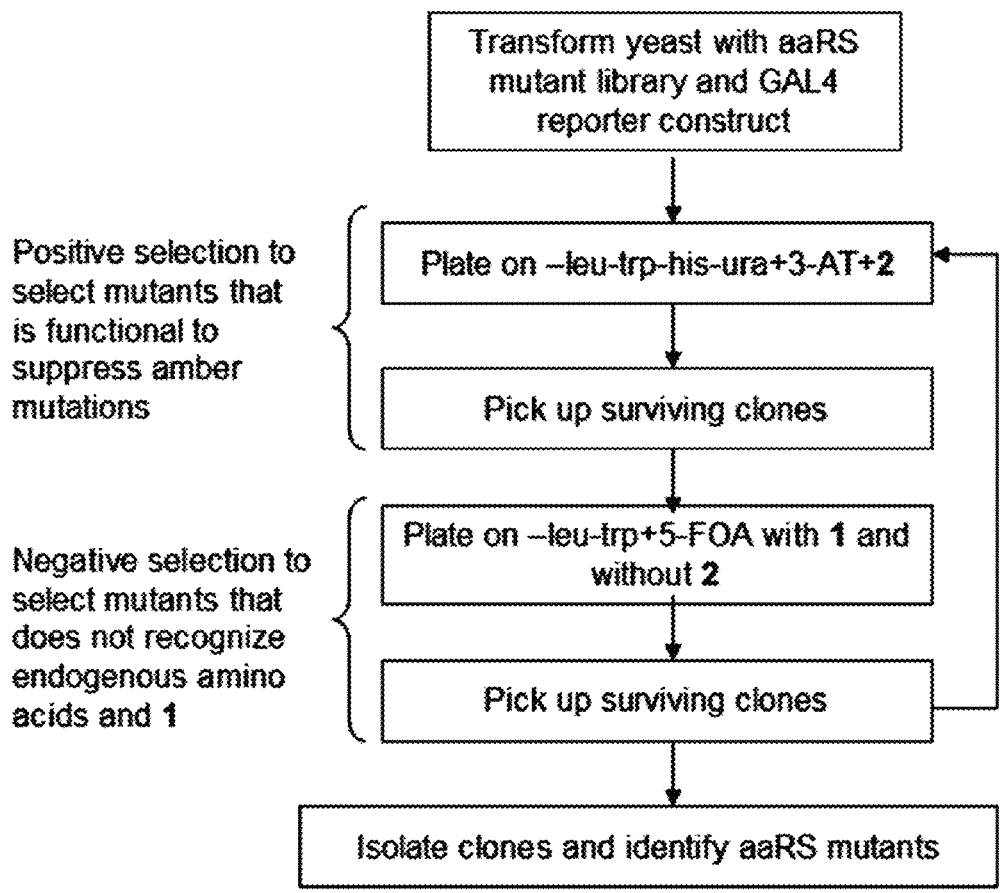
FIG. 12 shows a selection process for incorporation of fluorescent amino acids.

In contrast to E1 and E2 which have only one isoform in human, E3 ligases are consisted of three distinct types of proteins: the PIAS [protein inhibitor of activated STAT (signal transducer and activator of transcription)] family, the polycomb group protein Pc2 and the nuclear pore complex protein RanBP2. Among the three types of E3 ligases, PIAS proteins have been most extensively studied. Human genome encodes four PIAS genes, PIAS1, PIAS3, PIASx and PIASy. PIAS proteins share a high sequence homology. They all feature a SP-RING domain, which is crucial for binding Ubc9, and a SUMO interaction motif (SIM) implicated in directly binding SUMOs. PIAS proteins were first identified by their ability to interact with and inhibit the transcriptional activity of STAT proteins. PIAS1 and PIAS3 interact with STAT1 and STAT3 respectively with high specificity. Later it was discovered that PIAS proteins can also function as SUMO E3 ligases to induce SUMOylation of the proteins they interact with. In the case of cytokine signaling pathway, binding of interferon gamma to its receptor leads to activation of STAT1, which translocates into nucleus and induces downstream gene expression. PIAS1 interacts with activated STAT1 and induces SUMOylation of STAT1 to inhibit its transcriptional activity, therefore ensuring proper regulation of interferon signaling (FIG. 4). Besides STAT proteins, PIASs can also promote SUMOylation of a variety of structurally diverse proteins. Most of these proteins are transcriptional factors including p53, whose transcriptional activity is strongly repressed by PIAS1-mediated SUMOylation.

While SUMOylation plays an important role in many biological processes including regulation of immune signal transduction, stabilization of target proteins and maintenance of chromosomal integrity, the investigation of SUMOylation network in vivo has been hindered by many challenges. Conjugation and deconjugation of SUMO is highly dynamic process and SUMO can be quickly removed upon cell lysis unless cells are lysed in denaturing conditions or protease inhibitors are added. Furthermore, given the important roles they play, gene knockout of components in SUMOylation can be lethal. Depletion of SUMO1 or the E2 enzyme in mice is embryonically lethal. PIAS1 deficient mice are partially embryonically lethal and the activity of their interferon-mediated JAK-STAT pathway is deregulated. To overcome these difficulties, new tools besides the traditional biochemical and genetic approaches are needed to study the SUMOylation network.

Among a variety of techniques for biological research, small chemical compounds stand as unique tools to manipulate the activity of biological processes. Compared with other biological approaches, bioactive small chemical compounds not only offer better spatial and temporal control of biological processes but also can be used to investigate the biological function of proteins when gene knockout studies are not feasible. While the majority of chemical compounds used in biological research are receptor agonists/antagonists or enzyme inhibitors, small chemical compounds disrupting non-enzyme protein-protein interactions have emerged as useful tools. Nutlin-3, an ubiquitin E3 ligase inhibitor developed in 2004, has been shown to induce apoptosis and growth inhibition of cancer cells by disrupting the interaction of ubiquitin E3 ligase MDM2 and its substrate p53. Analogous to ubiquitination, SUMOylation requires interactions between SUMO, catalyzing enzymes and substrate proteins.

Therefore small chemical compounds disrupting interactions between components in SUMOylation will be very useful to dissect the whole network. Currently there is no available small chemical compound specific for SUMOylation pathways, which indicates an urgent need in developing high-throughput screening assays for these small molecule inhibitors.

The disclosure also provides methods and compositions using FRET (Förster resonance energy transfer)-based high-throughput screening to identify small chemical inhibitors which can specifically disrupt protein-protein interaction involved in the SUMOylation network. FRET occurs between two adjacent fluorophores when their distance is smaller than 1-10 nm and the emission spectrum of donor has more than 30% overlapping with the excitation spectrum of acceptor. Energy transferred from excited donor to acceptor results in quenching of donor and excitation of acceptor (FIG. 1). Because the efficiency of energy transfer is highly dependent (sixth-power) on the distance between donor and acceptor fluorophores, FRET-based techniques have been extensively used in biological research including identification of protein interactions, real-time monitoring of intracellular signaling activities, and high-throughput screening of bioactive molecules. Compared with traditional techniques used to identify protein-protein interactions such as co-immunoprecipitation and yeast two-hybrid, FRET is able to offer real-time monitoring in living cells and is easier to be adapted into high-throughput screening. In FRET-based assays, proteins are tagged with different fluorophores to form FRET pairs. Interaction of proteins recruits fluorophores together and increase the efficiency of energy transfer from donor fluorophores to acceptor fluorophores. Disruption of protein-protein interactions by small chemical inhibitors will separate the fluorophores apart and result in decreased FRET efficiency of the system.

Examples

Construct Mammalian Expression Constructs of FRET Reporter Protein

The expression plasmid expressing chimeric protein YFP-STAT1-KDJAK1-PIAS1*, and as negative control, YFP-STAT1-PIAS1* in mammalian cells were constructed in pcDNA3 (Invitrogen). The kinase domain of JAK1 phosphorylates the STAT1 and the phosphorylation of STAT1 initiates the interaction between PIAS1 and STAT1. Amber codon* is introduced into different positions of PIAS1 for later incorporation of L-(7-hydroxycoumarin-4-yl)ethylglycine. The constructs was transfected into HEK 293 cells and the fluorescent amino acid incorporation will be carried out. The cells were excited at 340 nm and fluorescence emission will be detected at 470 nm (for cells expressing YFP-STAT1-PIAS1*) or 527 nm (for cells expressing YFP-STAT1-KD-JAK3-PIAS1*) in the fluorescence plate reader, and cells without transfection are used as negative control.

Different organic fluorophores can be selected based on their excitation/emission spectrums and covalently conjugated to the backbone of amino acids. Orthogonal tRNA/aminoacyl-tRNA synthetase pairs will be screened. The resulting fluorescent amino acids will be incorporated into proteins individually and their FRET efficiency with L-(7-hydroxycoumarin-4-yl)ethylglycine will be measured.

As a testing of the developed assay of screening small molecular inhibitor(s), a pilot screening using the small molecular compound library containing 10,000 Benzopyran-like molecules will be performed. More libraries are available from the Genomic Institute at UCR. The cells will be transfected and spotted into 96- or 384-well plates and incubated for proper time and FRET assay will be performed. The candidates showing decreased FRET efficiency will be picked up for further analysis.

As a testing of the developed assay of screening small molecular inhibitor(s), a pilot screening using the small molecular compound library containing 10,000 Benzopyran-like molecules will be performed. More libraries are available from the Genomic Institute at UCR. The cells will be transfected and spotted into 96- or 384-well plates and incubated for proper time and FRET assay will be performed. The candidates showing decreased FRET efficiency will be picked up for further analysis.

SUMO1, Ubc9 and PIAS1 have been cloned from human cDNA library using polymerase chain reactions (PCR).

Cloning of Genes Encoding Proteins Involved in the SUMOylation Network into Mammalian Expression Vectors:

The open reading frames encoding SUMO1-4, SENP1-7 and PIAS1, 3, x, y will be amplified using PCR reactions from human cDNA library. The PCR products will be cloned into pCRII-TOPO vectors using the TOPO TA cloning kit (Invitrogen, CA) and sequenced for clones with correct sequences. The open reading frames of SUMOs will then be ligated into pCRII vectors encoding CyPet while the other genes will be ligated into pCRII encoding YPet. The CyPet and YPet fusion constructs will be transferred to mammalian expression vectors pcDNA3.1-hygromycin and pcDNA3.1-V5His (Invitrogen, CA) respectively.

Transfection of HEK293 Cells and Determination of FRET Emission Ratio of Transfected Cells:

$5 \times 10^4$ per well HEK293 cells will be plated in 12-well tissue culture plate in 0.5 mL Dulbecco's Modified Essential Medium (DMEM) supplemented with 10% fetal bovine serum (FBS) (Invitrogen, CA). After overnight incubation the cells will be transiently cotransfected with 1 ug plasmid encoding a CyPet fusion protein and 1 ug plasmid encoding a YPet fusion protein using FuGene6 (Roche, Switzerland) for 24 h in triplicate groups. Culture medium will then be aspirated and replaced with 50 μL phosphate buffered saline (PBS). Cells will be scraped off using a cell scraper (Fisher Scientific, PA) and the cell suspension will be transferred into a 384-well black/clear plate (BD bioscience, CA). The plate will be read on our fluorometric high-throughput plate reader (Flexstation II$^{384}$) instrument (Molecular Devices, CA). Two settings will be used to detect the fluorescence emitted from transfected cells: excitation at 414 nm with a long-pass cutoff filter at 455 nm and emission at 475 nm and 530 nm; excitation at 465 nm with a long-pass cutoff filter at 495 nm and emission scan at 530 nm. The settings are adjusted to excite and detect at the appropriate wavelengths for each fluorophore. For example, $FLC_{DD}$: FLC at 465 nm under excitation at 414 nm with a long-pass cutoff filter at 455 nm;

$FLC_{DA}$: FLC at 530 nm under excitation at 414 nm with a long-pass cutoff filter at 455 nm;

$FLC_{AA}$: FLC at 530 nm under excitation at 465 nm with a long-pass cutoff filter at 495 nm;

The FRET emission ratio (r) was defined to be the ratio of corrected fluorescence intensities at 530 nm and 475 nm under excitation at 414 nm:

$$r = FLC_{DA}/FLC_{DD} \qquad (1)$$

Because energy transfer from the donor fluorophore to the acceptor fluorophore will result in an increase of r, increased r can serve as an indication of FRET. A cross-talk constant can be determined for cells expressing only one type of fluorophore:

$$a = FLC_{DA}/FLC_{AA} \quad (2)$$

Then the modified equation of r will be:

$$r = \frac{FLC_{DA} - a \times FLC_{AA}}{FLC_{DD}} \quad (3)$$

in which $a \times FLC_{AA}$ reflected the direct emission. r will be determined for different pairs of fluorophores. They will then be compared with the ratio from the control group in which the cells will be transfected with plasmids encoding labeled constructs. The student t test will be used to check if the FRET emission ratios of tested protein pairs have statistically significant differences with that from the control group. The positive pairs showing an increase of r will be subject to further testing described below.

Estimation of Protein-Protein Binding Affinities in Living Cells Using FRET Measurements:

$5 \times 10^4$ HEK293 cells will be plated into 12-well plate and transfected with plasmids encoding the fusion protein pairs using the protocol described above. After the cells are suspended and transferred into a 384-well black/clear plate, the corrected fluorescence intensities of the cells will be determined in Flexstation II$^{384}$. Because of the overlapping of CyPet and YPet fluorescence spectra, all these intensities are consisted of three components: the donor (CyPet) fluorescence ($I_d$), the sensitized acceptor (YPet) fluorescence due to FRET ($I_{da}$), and the acceptor (YPet) fluorescence ($I_a$). To isolate these components, $FLC_{DD}$, $FLC_{DA}$ and $FLC_{AA}$ from HEK293 cells expressing only YPet will be measured. The following cross-talk constants will be determined as:

$$a = \frac{FLC_{DA}}{FLC_{AA}}$$

$$b = \frac{FLC_{DD}}{FLC_{AA}}$$

The $FLC_{DD}$, $FLC_{DA}$ and $FLC_{AA}$ from HEK293 cells expressing only CyPet can be measured and determine the cross-talk constants for CyPet:

$$c = \frac{FLC_{AA}}{FLC_{DD}}$$

$$d = \frac{FLC_{DA}}{FLC_{DD}}$$

The corrected fluorescence intensities of the transfected cells will be characterized by the following equations:

$$FLC_{DD} = I_d + \left(\frac{b}{a}\right)I_{da} + bI_a$$

$$FLC_{DA} = dI_d + I_{da} + aI_a$$

$$FLC_{AA} = dI_d + \left(\frac{c}{d}\right)I_{da} + I_a$$

In these equations $I_d$ refers to the CyPet fluorescence at 475 nm under excitation of 414 nm. $I_{da}$ is the FRET-induced YPet emission at 530 nm under excitation of 414 nm. $I_a$ is the direct YPet fluorescence at 530 nm under excitation of 465 nm. From these equations $I_d$, $I_{da}$, and $I_a$ as functions of $FLC_{DD}$, $FLC_{DA}$ and $FLC_{AA}$ can be obtained:

$$I_a = \frac{(dFLC_{AA} - cFLC_{DA})}{(d - ca)}$$

$$I_d = \frac{(aFLC_{DD} - bFLC_{DA})}{(a - bd)}$$

$$I_{da} = FLC_{DA} - aI_a - bI_b$$

To convert $I_d$, $I_{da}$, and $I_a$ into FRET efficiency (E) and total concentrations of the donor (D) and the acceptor (A), two factors need to be determined: 1) The ratio of sensitized acceptor emission to donor fluorescence quenching (G factor) and 2) The ratio of donor/acceptor fluorescence intensities under equimolar concentrations in the absence of FRET (k factor). After the G and k factors were determined for CyPet and YPet under our experiment conditions, FRET efficiency E and the concentration ratio $$\frac{D}{A}$$

can be determined as:

$$E = \frac{\frac{I_{da}}{G}}{I_d + \frac{I_{da}}{G}}$$

$$\frac{D}{A} = \frac{I_d + \frac{I_{da}}{G}}{I_a k}$$

$I_a$ is used to present the relative concentration of the acceptor (A) because $I_a$ is not altered by FRET and is proportional to the concentration of the donor:

$$A = I_a$$

Then the relative concentration of the donor (D) can be represented as:

$$D = \frac{I_d + \frac{I_{da}}{G}}{k}$$

HEK293 cells will be transfected with varying amount of plasmids. $I_d$, $I_{da}$ and $I_a$ will be calculated for each batch of transfected cells from $FLC_{DD}$, $FLC_{DA}$ and $FLC_{AA}$ determined by Flexstation II$^{384}$. E and the $$\frac{D}{A}$$

will be also calculated to estimate the equilibrium dissociation constant $K_d$ following the protocol described below.

The behavior of the bimolecular interaction between donor and acceptor molecules can be described by the following equations based on receptor-ligand binding theories:

$$D_{free} + A_{free} \Leftrightarrow DA$$

$$D = D_{free} + DA$$

$$A = A_{free} + DA$$

$$K_d = \frac{D_{free} A_{free}}{DA} = \frac{(D - DA)(A - DA)}{DA}$$

$D_{free}$, $A_{free}$ and DA in the equations stand for the concentrations of free donor, free acceptor and binding complex of donor-acceptor, respectively. At equilibrium, DA can be represented as the function of D, A and $K_d$:

$$DA = \frac{(A + D + K_d) - \sqrt{(A + D + K_a)^2 - 4AD}}{2}$$

Then the predicted FRET efficiency $E_{pred}$ in a two-molecule system can be described as:

$$E_{pred} = E_{max} \times \frac{DA}{D}$$

$E_{max}$ is defined as the intrinsic FRET efficiency between a given pair of FRET donor and acceptor which is the FRET efficiency when all the FRET donor molecules are occupied by the acceptor molecules. Combining yields:

$$E_{pred} = E_{max} \times \frac{(A + D + K_d) - \sqrt{(A + D + K_d)^2 - 4AD}}{2D}$$

For cells expressing varying amounts of fusion protein pairs, A and D can be determined based on the methods described above. Thus two unknown independent variables $E_{max}$ and $K_d$ need to be estimated and adjusted to minimize the difference between the predicted FRET efficiency ($E_{pred}$) and experimentally determined FRET efficiency (E). Assuming $E_{pred}$ having a Gaussian distribution, based on maximum likelihood analysis the best estimation of $K_d$ and $E_{max}$ results in a minimized squared residual error (SEE) which is defined as:

$$SEE = \Sigma(E - E_{pred})^2$$

The SSE of a matrix of hypothetical $K_d$ and $E_{max}$ values will be calculated on the computer as described. The $E_{max}$ and $K_d$ of the protein pair expressed in HEK293 cells will then be estimated based on the $SEE_{min}$. The critical value of the SSE for P=0.05 can be determined as described so the 95% confidence intervals of $E_{max}$ and $K_d$ can be estimated. The $K_d$ of different protein pairs will be compared to see if different members of SUMO-specific peptidases and SUMO E3 ligases favor interactions with different SUMO peptides.

FRET can be used to detect protein-protein interactions in the SUMOylation network and to estimate the binding affinities of different protein pairs in living cells. The FRET emission ratio, which is the ratio of fluorescence intensity at the emission peak of the acceptor and the donor under excitation of the donor, can serve as judging criteria for the occurrence of FRET. Our preliminary studies have shown that the interaction of SUMO1 and Ubc9 results in a change of FRET ratio when they are tagged with CyPet and YPet respectively. Changes in the FRET emission ratio are expected to be seen for more protein pairs as interactions between many proteins involved in the SUMOylation pathway have been proved. Positive protein pairs which show an increase of FRET emission ratio compared with the control group will be identified and the disassociation constant $K_d$ of the protein pairs will be estimated by subtracting cross-talk components from fluorescent spectra followed by a computationally intense prediction of $K_d$ and $E_{max}$ based on the least-square methods. Binding affinities of SUMO-specific peptidases and SUMO E3 ligases (in our case PIASs) will differ towards different members of SUMO peptides. The comparison of their $K_d$ with different SUMO peptides will give us information about their specificities in the SUMOylation and deSUMOylation processes, which is still not fully understood.

The efficiency of FRET is highly dependent on the distance between the donor and acceptor to the power of six. The Förster distance of fluorescent proteins is around 40-50 Å, which is comparable with the size of protein molecules. Therefore the FRET efficiency of two fusion proteins in our assay is highly dependent on the conformation of the fusion protein complexes. Conjugation of CyPet/YPet onto different sites of target proteins such as the N- or C-terminus will change the distance between two fluorescent proteins. As a result, while the occurrence of FRET signal indicates the interaction of two fusion proteins, lack of FRET signal does not necessarily mean the tested fusion proteins do not interact with each other. It is possible that even when two tested proteins interact in living cells, the conjugated fluorescent proteins are still separated by a long distance which makes the FRET signal too small to be detectable under our experimental settings.

It should be noticed that because the concentrations of the donor and the acceptor are measured in units of fluorescence rather than concentration units, estimated $K_d$ will be expressed in units of fluorescence (RFU, Reference Unit) as well. The result is dependent on the setting of the instrument such as the power of the laser and the sensitivity of the sensor. In order to compare the estimated $K_d$ between different protein pairs, FRET measurements of transfected mammalian cells must be carried out under the same experimental setting. While the estimated $K_d$ does not have a concentration unit, the estimated $K_d$ can be calibrated with the literature value from in vitro studies if it is assumed that in vivo and in vitro binding affinities are comparable. SUMO1-Ubc9 can be set as a standard.

In another embodiment, the disclosure provides FRET constructs to screen small chemical inhibitors of protein-protein interactions in the SUMOylation network. As the interaction of CyPet/YPet-conjugated proteins recruits two fluorescent proteins together and results in FRET, small chemical compounds disrupting their interaction will separate the fluorescent proteins apart and decrease the efficiency of FRET. HEK293 cell lines stably expressing CyPet/YPet fusion proteins will be developed. Small chemical libraries will be added onto the stable cell lines and compounds decreasing the ratiometric FRET signal will be picked up for further analysis.

$5 \times 10^4$ per well HEK293 cells will be plated in 12-well tissue culture plate in 0.5 mL DMEM supplemented with 10% FBS. After overnight incubation a pair of expression vectors encoding CyPet and YPet fusion proteins respectively which shows an increased FRET ratio will be used to transfect the cells with FuGene6. 24 h after transfection, cells will be washed by PBS and detached from the plate by trypsin. The suspended cells will then be split into 15 cm tissue culture plate in 10 mL DMEM supplemented with 10% fetal bovine serum. Hygromycin and geneticin (Invitrogen, CA) will be added into the media the next day to a concentration of 150 µg/mL and 750 µg/mL, respectively. Cell culture medium will be refreshed every 3-4 days to remove dead cells until the living cells forms visible colonies in the plates. The stable cell colonies will be transferred into 96-well plates and their fluorescence emission at 475 nm and 530 nm will be determined under excitation at 414 nm and 465 nm respectively. The colonies with good expression of both proteins will be selected and serve in the test group in the screening assay described below. Control cell lines expressing different isoforms can be generated as the specificity control group for the high through-put screening assay. Taking cells expressing CyPet-SUMO and YPet-PIAS1 as an example, the specificity control group will be stable cell lines expressing CyPet-SUMO1 and YPet-PIAS3/x/y.

Optimization of the Assay and High-Throughput Screening of Small Chemical Inhibitors:

Z factor has been widely used to assess the quality of high-throughput screening assays. It is determined by the variability in sample data as well as the dynamic range between the high and low data populations. Z factor is defined as follows:

$$Z = 1 - \frac{(3\sigma_s + 3\sigma_c)}{|\mu_s - \mu_c|}$$

$\mu_s$ and $\mu_c$ are the means of the samples and control populations, respectively. $\sigma_s$ and $\sigma_c$ are designed as their standard deviation. Z factor is a dimensionless factor between −1 and 1. It approaches 1 as the variability of the data approaches 0 or the dynamic range of the assay approaches infinity. To estimate the dynamic range and standard deviation of positive hits, the stable cell lines will be transfected with unconjugated acceptor proteins. Taking the HEK293 cells stably expressing CyPet-SUMO1 and YPet-Ubc9 as an example, cells will be transfected with different amount of unconjugated Ubc9. The unconjugated Ubc9 will compete with fluorescent protein-tagged Ubc9 and decrease the FRET ratio of transfected cells. Transfected or untransfected stable cell lines and mock transfected HEK293 cells will be trypsinized, resuspended in PBS and aliquoted into 384-well plates with various cell densities. The fluorescence intensities at 475 nm and 530 nm from each well will be determined by Flexstation II$^{384}$ under excitation at 414 nm and subtracted by those from the mock transfected cells. Z factor will be determined for each cell line at each cell density per well. The setting showing the highest Z factor will be used for the screening assay.

For the high-throughput screening, cells in the test group as well as mock transfected HEK293 cells will be aliquoted into 384-well plate based on the optimized setting and small chemical compounds or vehicles will be added into each well to a final concentration of 1 µM. Compounds can be added to mock transfected HEK293 cells as the background group. After incubation at 37° C. for 1 h, fluorescence intensities of each well will be determined as described above and subtracted by those from the background group. The FRET emission ratio (r) and FRET efficiency (E) will then be calculated based on the algorithms described above and compared with those from the untreated stably transfected cells. The compounds showing a statistically significant decrease of r or E will be picked up and can be further tested in the specificity control group to determine the specificity of their effects.

Cells stably expressing FRET protein pairs will be generated. Z factor as a criterion of assay quality will be determined for the best setting of the high-throughput screening assay. Small chemical library will be applied to cells and the fluorescence intensity from each well will be determined. The FRET emission ratio and FRET efficiency of each well can be calculated and compounds which decreases these two parameters will be picked up and their specificity can be determined in the specificity control group. At the conclusion of these proposed experiments, potential small chemical inhibitors will be selected based on their ability to disrupt the interaction between the tested protein pair, which can be validated by the biological assays described herein.

In the assay decrease of FRET signals can be achieved by not only inhibitors disrupting protein-protein interactions, but also fluorescence quenchers. Quenching of YPet fluorescence will result in a decreased YPet sensitized emission regardless of the binding status of the FRET protein pair. Therefore it is necessary for the positive hits from the high-throughput screening to be further characterized by fluorescence-independent techniques in order to rule out the false positives.

The small chemical libraries used in the screening may contain fluorescent compounds whose excitation spectrum overlaps with that of CyPet. The direct emission from these fluorescent compounds will interfere with the calculation of FRET efficiency between the FRET protein pair. In the background control group of our assay, compounds are added into mock transfected cells so both the autofluorescence of the cells and the fluorescence of compounds can be subtracted from the readings of test groups.

To develop secondary biochemical and biological assays to validate and characterize potential small chemical inhibitors which specifically disrupt the interaction between proteins involved in the SUMOylation network. The inhibitors picked up from FRET-based high-throughput screening maybe specific inhibitors disrupting protein-protein interaction or simply fluorescence quenchers so it will be necessary to develop secondary assays to validate their activities. The methods of the disclosure include the use of coimmunoprecipitation assays, yeast two-hybrid tests and in vitro SUMOylation assays. In these assays, disruption of protein-protein interaction by addition of specific inhibitors will lead to decreased coimmunoprecipitation, changing of yeast phenotype or inhibition of in vitro SUMOylation. In the following experiment design session, the CyPet-SUMO1/YPet-PIAS1 pair will be used as an example to demonstrate these assays in the validation of small chemical inhibitors disrupting the interaction between SUMO1 and PIAS1. The potential inhibitors of other protein pairs can be analyzed following similar protocols.

To Validate Small Chemical Inhibitors Using SUMO1/PIAS1 Coimmunoprecipitation Assay:

HEK293 cells will be transfected with plasmids encoding SUMO1 and PIAS1 using protocols described previously. After 48 h incubation, cells will be lysed by RIPA lysis buffer and the supernatant after centrifugation will used for the immunoprecipitation assay. The potential chemical inhibitor candidates will be added into the supernatant to different final concentrations before SUMO1/PIAS1 complex is precipitated by anti-SUMO1 antibodies. The amount of coimmunoprecipitated PIAS1 will be analyzed by western blots with anti-PIAS1 antibodies. The intensity of PIAS1 on western blots will be quantified and plotted against the final concentration of the inhibitor in the supernatant to determine the IC$_{50}$ of the inhibitor, at which the amount of precipitated PIAS1 is decreased by 50%.

To Validate Small Chemical Inhibitors Using Yeast Two-Hybrid Assay:

The ProQuest™ two-hybrid system (Invitrogen, CA) will be used in the assay. In this system, the gene encoded in the bait vector and the prey vector will be fused with the open reading frame of GAL4 DNA binding domain and GAL4 activation domain respectively. After the plasmids are transformed into the yeast cells, bait and prey proteins will be expressed and their interaction will recruit the GAL4 DNA binding domain and activation domain together and drive the expression of auxotrophic markers including HIS3 and URA3. Therefore the interaction of tested proteins can be detected by the changes in the phenotype of transformed yeast cells. In the experiment, SUMO1 and PIAS1 will be cloned into the bait and prey expression vectors and transformed into the Mav203 yeast strain following the protocol provided in the kit. 5-fluoroorotic acid (5FOA) is a chemical compound which is converted to a toxic compound in the presence of URA3. Therefore the interaction of SUMO1 and PIAS1 will lead to the death of transformed yeast cells when they are plated on medium containing 5FOA. The potential chemical inhibitor candidates will be added onto the transformed yeasts to determine if they can disrupt the interaction of SUMO1 and PIAS1 in yeast cells to rescue the transformed yeasts on medium containing 5FOA. Alternatively, because the expression of HIS3 and URA3 will allow cells to grow in the absence of histidine and uracil, the small chemical inhibitors can be added onto transformed yeast cells plated on medium lacking histidine and uracil to determine if they can inhibit the growth of transformed yeast cells.

To Validate Small Chemical Inhibitors Using In Vitro SUMOylation Assay:

It is necessary to directly determine the effects of small chemical inhibitors on the SUMOylation process. The heterodimeric E1, Uba2 and Aos1, will be expressed and purified from bacteria. Ubc9, SUMO1 and STAT1 can be purified from bacteria. Flag-tagged PIAS1 protein will be obtained from mammalian cells. The assay will be performed in a mixture containing purified proteins of Uba2/Aos1, Ubc9, SUMO1, PIAS1 and STAT1 in an ATP regenerating buffer (50 mM Tris-HCl at pH 7.6, 5 mM $MgCl_2$, 2 mM ATP, 10 mM creatine phosphate, 3.5 U/ml creatine kinase, and 0.6 U/ml inorganic pyrophosphatase, 1x protease inhibitor cocktail) in the presence or absence of various concentrations of inhibitors. Reaction mixtures will be incubated at 37° C. and analysed by western blots with anti-SUMO1 or anti-STAT1 antibodies. ICH of the inhibitors can be determined when the secondary antibody is labeled with fluorescence and the fluorescence is quantified with fluorescence reader.

The major goal of the experiments is to establish a series of secondary biological assays that can be used to confirm and validate potential small chemical inhibitors disrupting protein-protein interaction in the SUMOylation pathway. In the first two assays two techniques commonly used to detect protein-protein interaction were used to test if the potential inhibitors can disrupt the interaction of their targets either in vitro or in vivo. In the third assay the effects of potential inhibitors on the SUMOylation process will be tested. At the conclusion of these experiments small chemical inhibitors which can disrupt the interaction of specific targets and manipulate the activity of the SUMOylation pathway are identified. These inhibitors will be subject to further analysis such as function-structure studies.

In the yeast two-hybrid assay, both forward and reverse two-hybrid assays are used. While in both cases addition of inhibitors disrupts the interaction of bait and prey proteins and inhibits the expression of HIS3 and URA3, in the forward two-hybrid assay this results in the inhibition growth of transformed yeast cells in the absence of histidine and uracil whereas in the reverse two-hybrid assay this results in the growth of transformed yeast cells in the presence of 5FOA. The reverse two-hybrid assay is better than the forward assay in that it not only avoids the false positive hits which kill yeast cells due to their cytotoxicity but also rules out the chemicals functioning as a general inhibitors for general transcriptional/translational machinery. However, the positive hits generated from both assays may change the phenotypes of transformed yeast cells by inhibiting the activities of HIS3 or URA3 proteins. Another potential problem is that the inhibitors may be able to get into the cytoplasm of mammalian cells but not yeast cells so false negative results will be given for these inhibitors in the yeast two-hybrid assays. Therefore the yeast two-hybrid assay must be supplemented by other assays to validate the activity and specificity of small chemical inhibitors identified as above.

To validate the inhibitors disrupting SUMO-SENP interaction, in vitro deSUMOylation assay are used. Myc-tagged SENP protein will be expressed and purified in mammalian cells. Purified SENP proteins will be mixed with in vitro SUMOylated STAT1. After incubation at 37° C., reaction product will be analyzed by SDS-PAGE with anti-SUMO1 and anti-STAT1 antibodies. Various concentrations of potential inhibitors will be added into the reaction mixture and test if they can inhibit the deSUMOylation of SUMOylated STAT1.

Synthesis of NBD amino acid and Fmoc-NBD amino acid

Scheme 1. Synhtesis of NBD amino acid derivative which can be used in solid phase peptide synthesis.

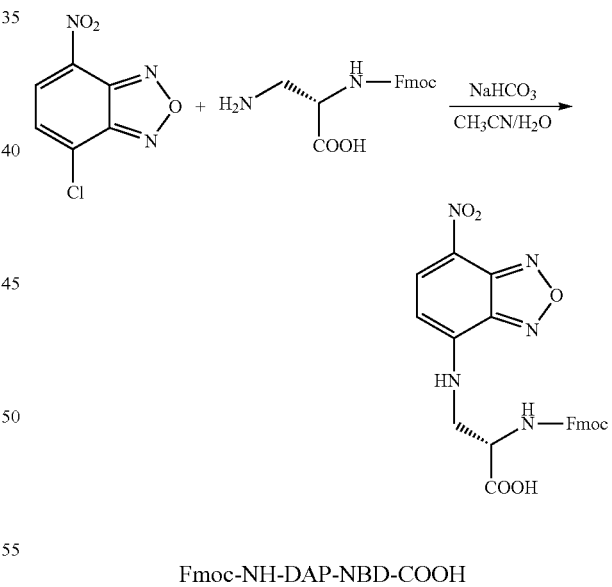

Fmoc-NH-DAP-NBD-COOH

To a stirred solution of sodium bicarbonate (0.154 g) and Nα-Fmoc, L-diamino propionic acid (0.5 g, 1.53 mmol) in 1:1 water and acetonitrile mixture (4 mL) was added 4-chloro-7-nitrobenzo-2-oxa-1,3-diazole (0.367 g, 1.836 mmol). The reaction mixture was allowed to stir overnight. Solvent was removed using rotary evaporation, and the remaining crude was purified by flash chromatograph on silica gel ($CH_2Cl_2$: MeOH=10:3) with trance acetic acid to give product as brown solid (0.482 g, 0.985 mmol, 64.3%). $^1$H NMR (400 MHz, DMSO, 25° C.) δ 3.80 (bs, 2H), 4.15 (t, J=8.4 Hz, 1H), 4.28 (d, J=9.2 Hz, 2H), 4.37 (m, 1H), 6.48 (d, J=11.6 Hz, 1H), 7.24 (t, J=9.6 Hz, 2H), 7.35 (m, 2H), 7.60 (d, J=10.0 Hz, 2H), 7.63 (d, J=10.4 Hz, 1H), 7.85 (d, J=10.0 Hz, 2H), 8.48 (d, J=10.4 Hz, 1H).

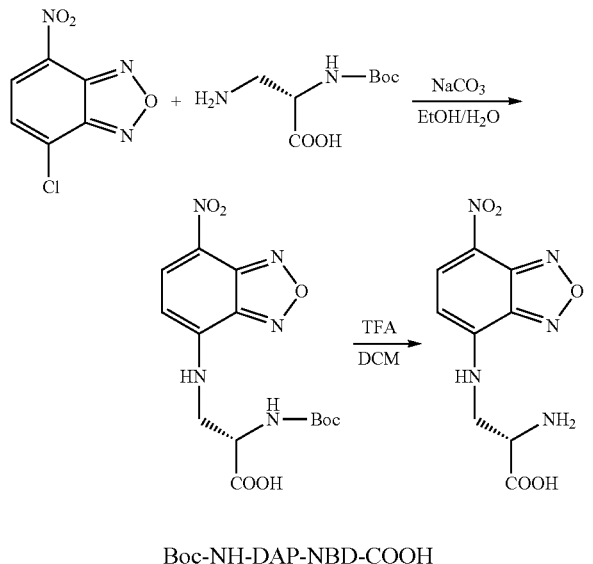

Scheme 2. Synthesis of NBD amino acid.

Boc-NH-DAP-NBD-COOH

To a stirred solution of sodium bicarbonate (0.049 g) and N-Boc-L-2,3-diaminopropanoic acid (0.1 g) in a 1:1 water and ethanol mixture was added 4-chloro-7-nitrobenzo-2-oxa-1,3-diazole (0.1 g) solution in 1:1 water and ethanol mixture. The reaction was allowed to stir overnight. Solvent was removed using rotary evaporation, and the remaining crude was dissolved in ethyl acetate and the product was extracted using a saturated sodium bicarbonate solution. The sodium bicarbonate fractions were combined and neutralized with concentrated acetic acid until a pH of 5-6 was achieved. The product N-[(1,1-dimethylethoxy)carbonyl]-3-[(7-nitro-2,1,3-benzoxadiazol-4-yl)amino]-L-alanine was extracted out of the aqueous solution using ethyl acetate. The combined ethyl acetate phase were dried over sodium sulfate, filtered, and the solvent removed by rotary evaporation. $^1$H NMR (300 MHz, DMSO, 25° C.) δ 1.39 (s, 9H), 2.70 (m, (m 1H), 3.00 (dd, J=4.8 Hz, J=11.7 Hz, 1H), 3.15 (bs, 2H), 3.59 (m, 1H), 6.15 (m, 1H), 8.20 (bs, 1H).

NH-DAP-NBD-COOH

Boc-NH-DAP-NBD-COOH was dissolved in methylene chloride and TFA was dropped slowly. The resulted solution was stirred under rt for 2.5 h. The solvent was removed under vacuum and afford the result product β-[(7-nitro-2,1,3-benzoxadiazol-4-yl)amino]-L-alanine $^1$H NMR (300 MHz, DMSO, 25° C.) δ 4.01 (m, 2H), 4.30 (m, 1H), 6.63 (d, J=8.7 Hz, 1H), 8.70 (bs, 2H).

Synthesis of Fmoc-CUM Amino Acid for Peptide Synthesis

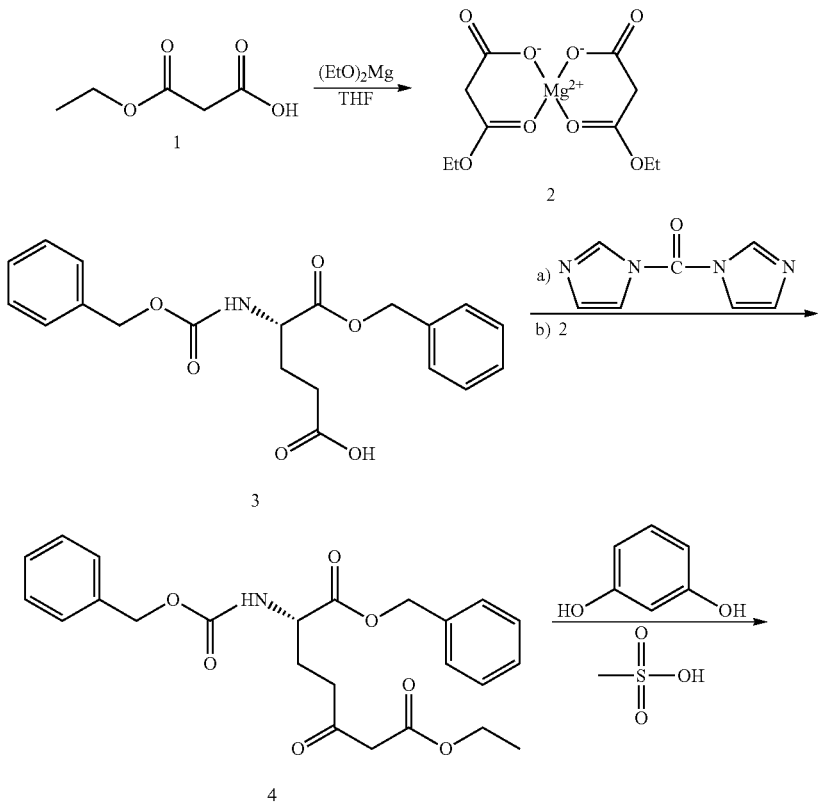

Scheme 3. Preparation of coumarin amino acid derivative which can be used in solid phase peptide synthesis.

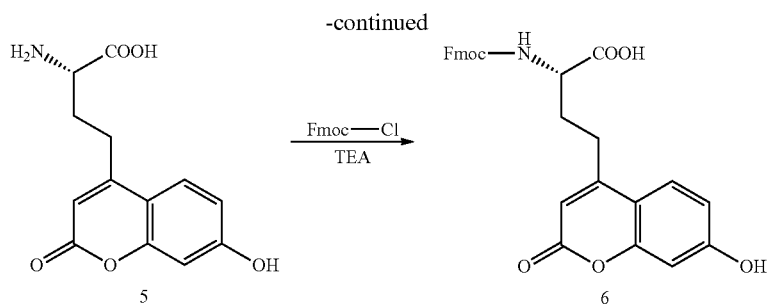

Ethyl Magnesium Malonate (2)

To a stirred solution of monoethyl malonate 1 (1.65 g, 12.5 mmol) in THF (25 mL) was added the magnesium ethoxide (0.61 g, 6.25 mmol). The reaction mixture was allowed to stir at rt for 5 h (until the solution become clear). The result solution was used for next step without any treatment.

(2S)-2-benzyloxycarbonylamino-5-oxo-heptanedioic acid 1-benzyl ester 7-ethyl ester (4)

Z-Glu-Obzl 3 (1.0 g, 2.7 mmol) was dissolved in dry THF (10 mL) at rt. Carbonyl diimidazole (0.48 g, 2.96 mmol) was added slowly and the mixture was then stirred for another 2 h. After the solution was cooled to 0° C., ethyl magnesium malonate solution 2 (4.7 mL, 1.2 mmol) was added, and the mixture was then stirred at rt overnight. The product was extracted with ester, and washed with 10% NaHCO$_3$, water, and brine. After the solvent was evaporated, the residue was purified by flash chromatography on silica gel (Hexanes: EtOAc=1:1) and afford a white solid (0.9 g, 2.03 mmol, 75.2%). $^1$H NMR (400 MHz, CDCl$_3$, 25° C.) δ 1.23 (t, 3H), 1.90-2.00 (m, 1H), 2.10-2.30 (m, 1H), 2.50-2.70 (m, 2H), 3.36 (s, 2H), 4.16 (q, 2H), 4.30-4.50 (m, 1H), 5.10 (s, 2H), 5.12 (s, 2H) 5.36 (m, 1H), 7.25-7.40 (m, 10H).

L-(7-hydroxycoumarin-4-yl)ethylglycine (5) 4

(0.24 g, 0.543 mmol) was added slowly to resorcinol (0.3 g, 2.73 mmol) in methanesulfonic acid (2 mL) at 0° C. and stirred for 3 h at rt. Ester (20 mL) was then added to the mixture and it was cooled to −30° C. The precipitate was washed with cold ether, dissolved in water, filtered, and lyophilized to get 5. $^1$H NMR (400 MHz, DMSO, 25° C.) δ 2.00-2.21 (m, 2H), 2.70-3.00 (m, 2H), 4.05 (m, 1H), 6.13 (s, 1H), 6.74 (d, 1H), 6.83 (dd, 1H), 7.62 (d, 1H), 8.33 (s, 3H).

L-Fmoc-amino-(7-hydroxycoumarin-4-yl)ethylglycine (6)

The coumaryl amino acid 5 (0.2 g, 0.557 mmol) dissolved in 4 mL 1:1 dioxane:water was treated at 0° C. with NaHCO$_3$ (0.187, 2.23 mmol). Then FmocCl (0.216, 0.836 mmol) was added at 0° C. and stirred at rt for 3 h. The reaction mixture was taken up in EtOAc, the organic extract was washed with water, 1N HCl and brine, dried over anhydrous Na$_2$SO$_4$. After the solvent was evaporated, the residue was purified by flash chromatography on silica gel (Hexanes:EtOAc=1:1) and afford a pale white solid (0.89 g, 0.183 mmol, 32.9%). $^1$H NMR (400 MHz, DMSO, 25° C.) δ 1.90-2.10 (m, 2H), 2.70-2.90 (m, 2H), 4.02 (m, 1H), 4.10-4.40 (m, 3H), 4.70 (d, 2H), 6.06 (s, 1H), 6.72 (s, 1H), 6.80 (d, 1H), 7.20-7.50 (m, 4H), 7.60 (d, 1H), 7.80-8.00 (m, 4H).

Peptide Synthesis

Synthesized peptide I (Ala-NBD-Ala-Gln-Thr-Gly-Gly-Ala-CUM-Gly; SEQ ID NO:8) and II (Tyr-Gly-Arg-Lys-Lys-Arg-Arg-Gln-Arg-Arg-Arg-Tyr-Pro-Tyr-Asp-Tyr-Pro-Asp-Try-Ala-NBD-Gln-Thr-Gly-Gly-CUM-Gly; SEQ ID NO:9) were carried out by contract synthesis from C S BIO (Menlo Park, CA.

Protein expression and purification. SENP2 gene was amplified using PCR and cloned in pET28(b) (Novagen. EMD Chemicals Inc. San Diego, Calif.). Recombinant SENP2 was expressed in bacteria strain B121(DE3) by 1 mM isopropyl-β-D-galactopyranoside (IPTG) at 37° C. for 4 h and was purified by nickel affinity chromatography under standard conditions.

Fluorescence Measurements.

Figure 13:
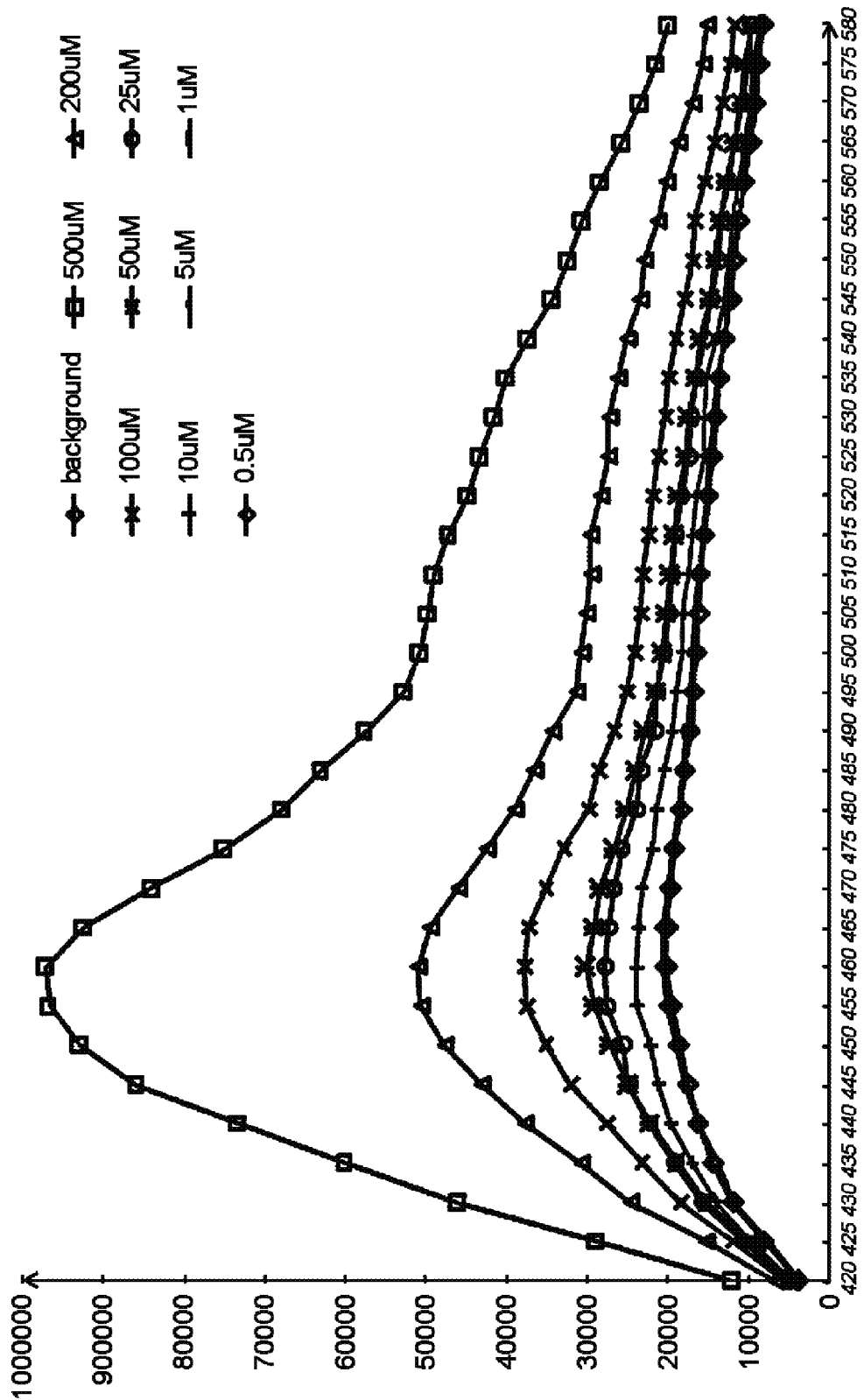
FIG. 13 shows the fluorescent intensity of peptide I solution with different concentration excited at 340 nm.

Various concentrations of the peptide I were dissolved in the buffer (25 mM Tris-HCl, 150 mM NaCl, 2 mM DTT, 0.1% Tween 20, modify pH at 8.0). Then the peptide solutions were transferred into 384 micro-well plate (Greiner Bio-one, New York, N.Y., US) at 30 μl/well. Fluorescent intensity was measured with 340 nm excitation wavelength (for coumarin) by FlexStation™ II[384] (Molecular Device, Sunnyvale, Calif., US). Results are shown in FIG. 13.

Figure 14:
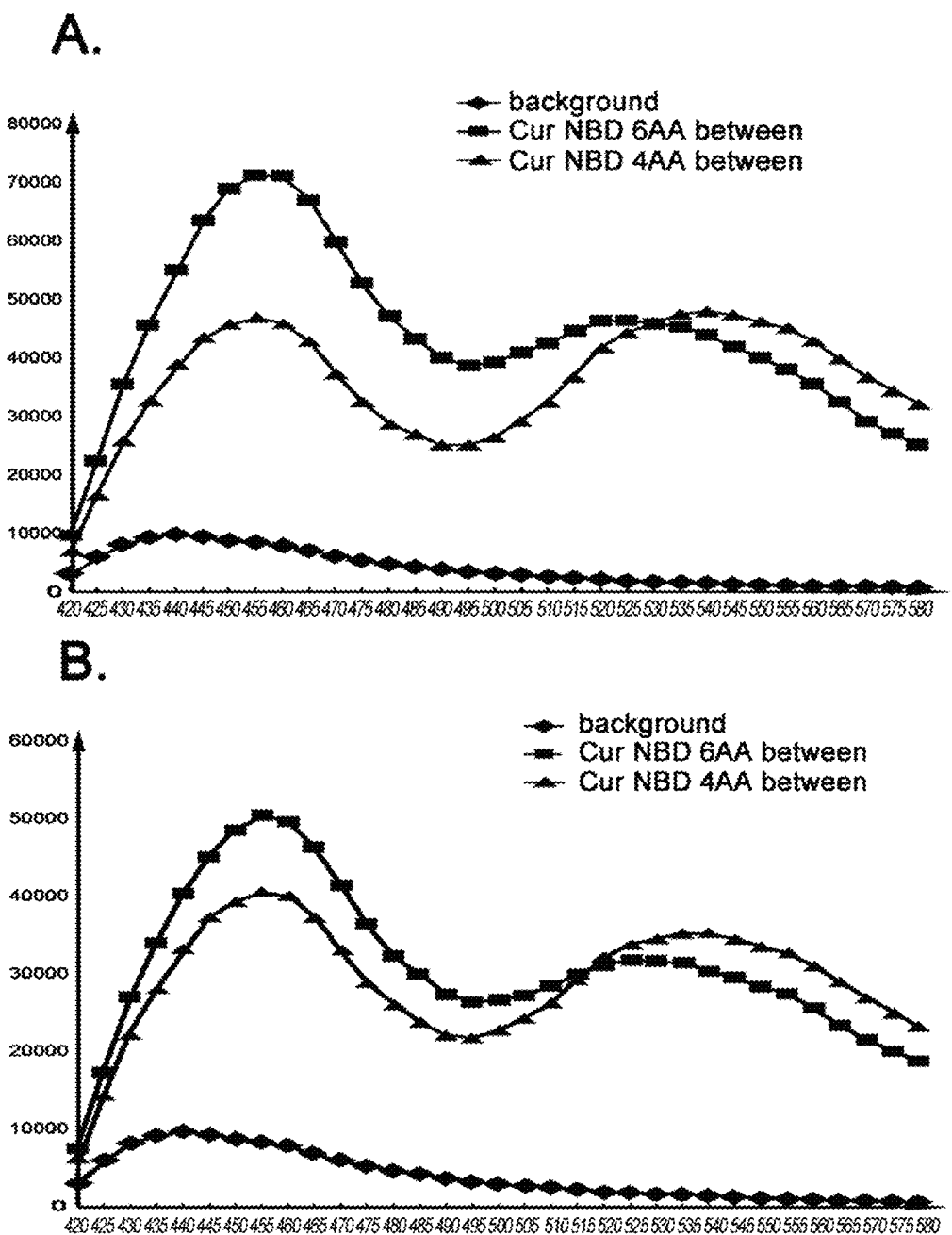
FIG. 14 shows fluorescent intensity of peptide I (6AA between coumarin and NBD) and II (4AA between coumarin and NBD) solution with different concentration (a: 200 μM; b: 100 μM.) excited at 340 nm.

Peptide I and II at various concentrations were aliquoted into 384 micro-well plate at 30 μl/well. FRET assay was measured by Flex StationII™[384] with the excitation wavelength of 340 nm. Result shows in FIG. 14.

Figure 15:
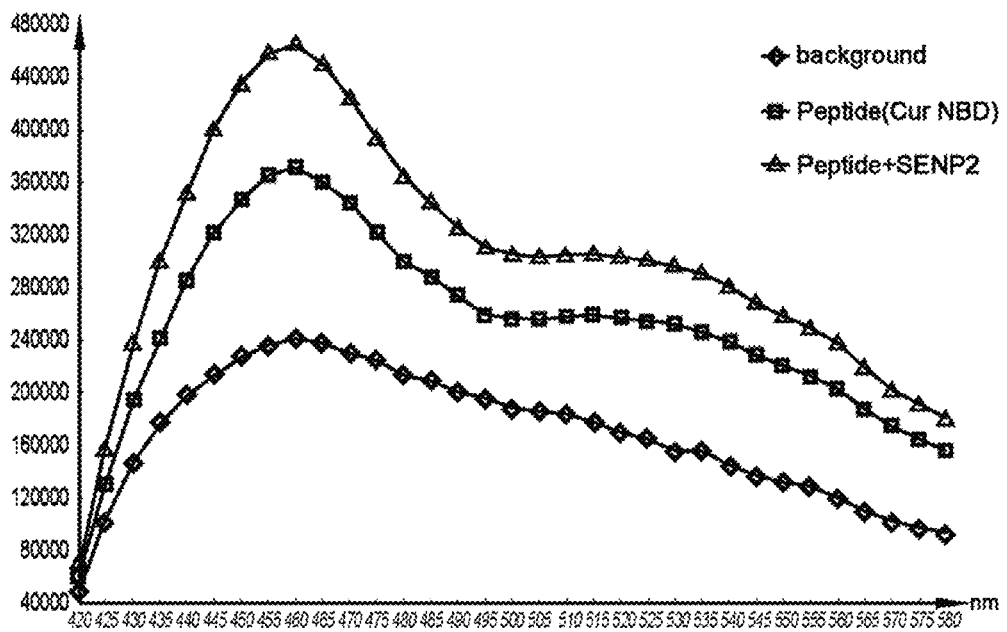
FIG. 15 shows fluorescent intensity of peptide I solution and interaction with SENP2 excited at 340 nm.

Peptide I solution was aliquoted into 384 micro-well plate at final concentration of 50 μM of 30 μl/well. Purified SENP2 was added to each well at final concentration of 15 μM. After the plate was gently agitated twice, the plate was sealed and incubated at 37° C. over night with aluminum foil covered. Fluorescent intensity was measured by FlexStation II™[384] the excitation wavelength of 340 nm. Result shows in FIG. 15.

Figure 16:
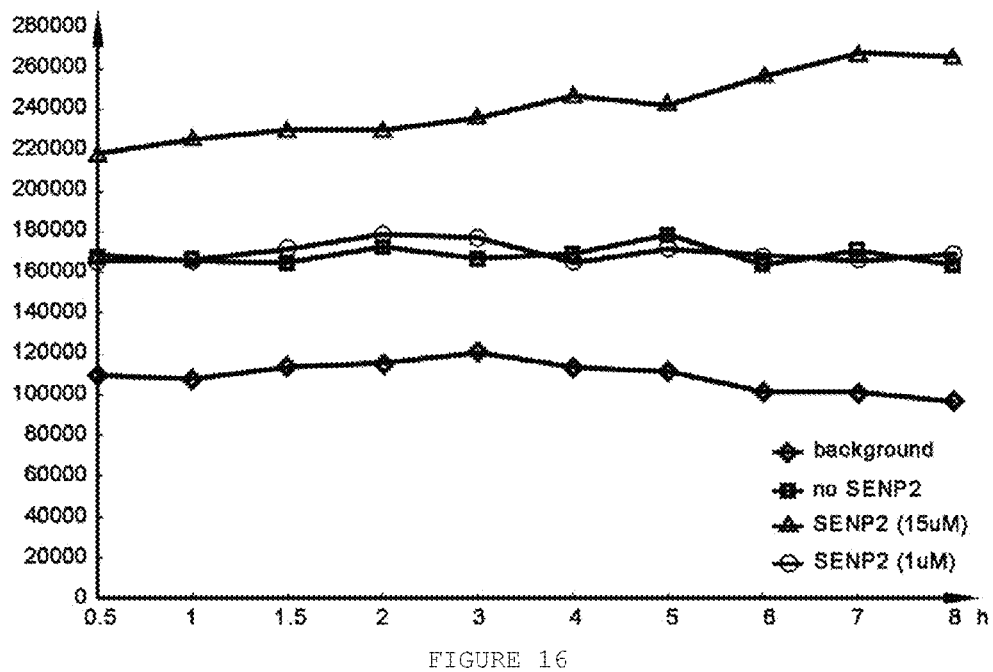
FIG. 16 shows fluorescent intensity of peptide I solution and interaction with SENP2 excited at 340 nm at different time point, checking at emission wavelength at 555 nm.

Peptide I solution was aliquoted into 384 micro-well plate at final concentration of 25 μM of 30 μl/well. Purified SENP2 was added to each well at different concentrations of 1 uM and 15 uM. After the plate was gently agitated twice and then the plate was sealed, the plate was covered with aluminum foil and incubated at 37° C. Fluorescent intensity was monitored by FlexStation II™[384] at excitation wavelength of 340 nm at different time point over the period of five hours. Result shows in FIG. 16.

As a novel application of fluorescent amino acid, this combination of protein engineering and high-throughput chemical screening will provide useful tools in SUMO studies but also provide ideas to other areas of biological research in which fluorescent amino acids and bioactive small chemicals can be used.

What is claimed is:

1. A polypeptide comprising:
   at least a first fluorescent amino acid comprising NBD (7-nitrobenzo-2-oxa-1,3-diazol-4-yl); and
   at least a second fluorescent amino acid comprising a coumarin fluorescent amino acid,
   wherein the at least first and second fluorescent amino acids are separated by 1, 2, 3, 4, 5, 6, 7, 8 or more amino acids and are capable of undergoing Föster resonance energy transfer (FRET).

2. The polypeptide of claim 1, wherein the at least second fluorescent amino acid prior to incorporation into the polypeptide and deprotection comprises structure IV:

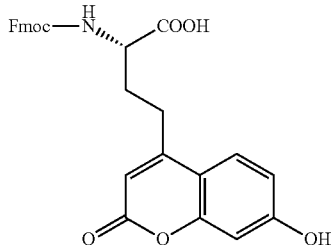

(IV)

and the at least first fluorescent amino acid prior to incorporation into the polypeptide and deprotection comprises structure V:

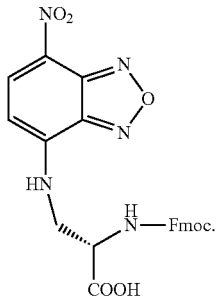

(V)

3. The polypeptide of claim 1, wherein the coumarin fluorescent amino acid is L-(7-hydroxycoumarin-4-yl)ethylglycine.

4. The polypeptide of claim 1, wherein the polypeptide is synthesized.

5. The polypeptide of claim 1, wherein the polypeptide is genetically expressed.

6. The polypeptide of claim 1, wherein the at least first and second fluorescent amino acids are separated by 4 to 6 amino acids.

7. The polypeptide of claim 1, wherein the at least first and second fluorescent amino acids are separated by about 10 nm or less.

8. The polypeptide of claim 1, wherein the at least first and second fluorescent amino acids are separated by a protease cleavage site.

9. The polypeptide of claim 1, wherein the polypeptide is fused to a cell penetrating peptide (CPP).

10. The polypeptide of claim 1, comprising the sequence Gln-Thr-Gly-Gly (SEQ ID NO:10) separating the first and second fluorescent amino acids.

11. A method of identifying a binding ligand or an enzyme for a target polypeptide, comprising:
    providing a polypeptide of claim 1, wherein the at least first fluorescent amino acid and the at least second fluorescent amino acid are capable of undergoing Förster resonance energy transfer (FRET); and
    measuring FRET in the presence and absence of the binding ligand or the enzyme, wherein a change in an emissions spectra is indicative that the polypeptide is bound by the ligand or a substrate for the enzyme.

* * * * *

SEQUENCE LISTING

<160> NUMBER OF SEQ ID NOS: 10

<210> SEQ ID NO 1
<211> LENGTH: 84
<212> TYPE: RNA
<213> ORGANISM: Artificial Sequence
<220> FEATURE:
<223> OTHER INFORMATION: tRNA sequence
<220> FEATURE:
<221> NAME/KEY: misc_feature
<222> LOCATION: (40)..(40)
<223> OTHER INFORMATION: N is a pseudouridine
<220> FEATURE:
<221> NAME/KEY: misc_feature
<222> LOCATION: (60)..(60)
<223> OTHER INFORMATION: N is a pseudouridine

<400> SEQUENCE: 1
ggagggguag cgaaguggcu aaacgcggcg gacucuaaan ccgcucccuu uggguucggn    60
cggcgaaucc gucccccucc acca                                          84

<210> SEQ ID NO 2
<211> LENGTH: 8
<212> TYPE: PRT
<213> ORGANISM: Artificial sequence
<220> FEATURE:
<223> OTHER INFORMATION: CPP consensus sequence
<220> FEATURE:
<221> NAME/KEY: MISC_FEATURE
<222> LOCATION: (1)..(1)
<223> OTHER INFORMATION: B is a basic amino acid
<220> FEATURE:
<221> NAME/KEY: MISC_FEATURE
<222> LOCATION: (2)..(4)
<223> OTHER INFORMATION: X is an alpha helix enhancing amino acid
<220> FEATURE:
<221> NAME/KEY: MISC_FEATURE
<222> LOCATION: (5)..(5)
<223> OTHER INFORMATION: B is a basic amino acid
<220> FEATURE:
<221> NAME/KEY: MISC_FEATURE
<222> LOCATION: (6)..(7)
<223> OTHER INFORMATION: X is an alpha helix enhancing amino acid
<220> FEATURE:
<221> NAME/KEY: MISC_FEATURE
<222> LOCATION: (8)..(8)
<223> OTHER INFORMATION: B is a basic amino acid

<400> SEQUENCE: 2

Asx Xaa Xaa Xaa Asx Xaa Xaa Asx
1               5

<210> SEQ ID NO 3
<211> LENGTH: 8
<212> TYPE: PRT
<213> ORGANISM: Artificial Sequence
<220> FEATURE:
<223> OTHER INFORMATION: CPP consensus sequence
<220> FEATURE:
<221> NAME/KEY: MISC_FEATURE
<222> LOCATION: (1)..(1)
<223> OTHER INFORMATION: B is a basic amino acid
<220> FEATURE:
<221> NAME/KEY: MISC_FEATURE
<222> LOCATION: (2)..(3)
<223> OTHER INFORMATION: X is an alpha helix enhancing amino acid
<220> FEATURE:
<221> NAME/KEY: MISC_FEATURE
<222> LOCATION: (4)..(5)
<223> OTHER INFORMATION: B is a basic amino acid
<220> FEATURE:
<221> NAME/KEY: MISC_FEATURE
<222> LOCATION: (6)..(7)

```
<223> OTHER INFORMATION: X is an alpha helix enhancing amino acid
<220> FEATURE:
<221> NAME/KEY: MISC_FEATURE
<222> LOCATION: (8)..(8)
<223> OTHER INFORMATION: B is a basic amino acid

<400> SEQUENCE: 3

Asx Xaa Xaa Asx Asx Xaa Xaa Asx
1               5

<210> SEQ ID NO 4
<211> LENGTH: 7
<212> TYPE: PRT
<213> ORGANISM: Artificial Sequence
<220> FEATURE:
<223> OTHER INFORMATION: CPP peptide

<400> SEQUENCE: 4

Lys Lys Arg Pro Lys Pro Gly
1               5

<210> SEQ ID NO 5
<211> LENGTH: 11
<212> TYPE: PRT
<213> ORGANISM: Artificial Sequence
<220> FEATURE:
<223> OTHER INFORMATION: CPP consensus sequence
<220> FEATURE:
<221> NAME/KEY: MISC_FEATURE
<222> LOCATION: (1)..(2)
<223> OTHER INFORMATION: X is any alpha helical enhancing amino acid
<220> FEATURE:
<221> NAME/KEY: MISC_FEATURE
<222> LOCATION: (4)..(4)
<223> OTHER INFORMATION: X is any alpha helical enhancing amino acid
<220> FEATURE:
<221> NAME/KEY: MISC_FEATURE
<222> LOCATION: (5)..(5)
<223> OTHER INFORMATION: X is any alpha helical enhancing amino acid or
      Proline
<220> FEATURE:
<221> NAME/KEY: MISC_FEATURE
<222> LOCATION: (6)..(6)
<223> OTHER INFORMATION: X is any alpha helical enhancing amino acid or
      a basic amino acid
<220> FEATURE:
<221> NAME/KEY: MISC_FEATURE
<222> LOCATION: (7)..(7)
<223> OTHER INFORMATION: X is a basic amino acid
<220> FEATURE:
<221> NAME/KEY: MISC_FEATURE
<222> LOCATION: (8)..(8)
<223> OTHER INFORMATION: X is any alpha helical enhancing amino acid or
      proline
<220> FEATURE:
<221> NAME/KEY: MISC_FEATURE
<222> LOCATION: (9)..(9)
<223> OTHER INFORMATION: X is any alpha helical enhancing amino acid
<220> FEATURE:
<221> NAME/KEY: MISC_FEATURE
<222> LOCATION: (10)..(10)
<223> OTHER INFORMATION: X is a basic amino acid
<220> FEATURE:
<221> NAME/KEY: MISC_FEATURE
<222> LOCATION: (11)..(11)
<223> OTHER INFORMATION: X is any alpha helical enhancing amino acid or
      a basic amino acid

<400> SEQUENCE: 5

Xaa Xaa Arg Xaa Xaa Xaa Xaa Xaa Xaa Xaa Xaa
1               5                   10

<210> SEQ ID NO 6
```

-continued

```
<211> LENGTH: 5
<212> TYPE: PRT
<213> ORGANISM: Artificial Sequence
<220> FEATURE:
<223> OTHER INFORMATION: CPP consensus sequence
<220> FEATURE:
<221> NAME/KEY: MISC_FEATURE
<222> LOCATION: (2)..(2)
<223> OTHER INFORMATION: X is R or K
<220> FEATURE:
<221> NAME/KEY: MISC_FEATURE
<222> LOCATION: (4)..(4)
<223> OTHER INFORMATION: X is any amino acid
<220> FEATURE:
<221> NAME/KEY: MISC_FEATURE
<222> LOCATION: (5)..(5)
<223> OTHER INFORMATION: X is R or K

<400> SEQUENCE: 6

Lys Xaa Arg Xaa Xaa
1               5

<210> SEQ ID NO 7
<211> LENGTH: 9
<212> TYPE: PRT
<213> ORGANISM: Artificial Sequence
<220> FEATURE:
<223> OTHER INFORMATION: CPP peptide

<400> SEQUENCE: 7

Arg Lys Lys Arg Arg Gln Arg Arg Arg
1               5

<210> SEQ ID NO 8
<211> LENGTH: 10
<212> TYPE: PRT
<213> ORGANISM: Artificial Sequence
<220> FEATURE:
<223> OTHER INFORMATION: Labeled peptide
<220> FEATURE:
<221> NAME/KEY: MISC_FEATURE
<222> LOCATION: (2)..(2)
<223> OTHER INFORMATION: X is a NBD amino acid
<220> FEATURE:
<221> NAME/KEY: MISC_FEATURE
<222> LOCATION: (9)..(9)
<223> OTHER INFORMATION: X is a CUM labeled amino acid

<400> SEQUENCE: 8

Ala Xaa Ala Gln Thr Gly Gly Ala Xaa Gly
1               5                   10

<210> SEQ ID NO 9
<211> LENGTH: 27
<212> TYPE: PRT
<213> ORGANISM: Artificial Sequence
<220> FEATURE:
<223> OTHER INFORMATION: Labeled peptide
<220> FEATURE:
<221> NAME/KEY: MISC_FEATURE
<222> LOCATION: (21)..(21)
<223> OTHER INFORMATION: X is an NBD amino acid
<220> FEATURE:
<221> NAME/KEY: MISC_FEATURE
<222> LOCATION: (26)..(26)
<223> OTHER INFORMATION: X is CUM labeled amino acid

<400> SEQUENCE: 9

Tyr Gly Arg Lys Lys Arg Arg Gln Arg Arg Arg Tyr Pro Tyr Asp Tyr
1               5                   10                  15

Pro Asp Tyr Ala Xaa Gln Thr Gly Gly Xaa Gly
```

```
<210> SEQ ID NO 10
<211> LENGTH: 4
<212> TYPE: PRT
<213> ORGANISM: Artificial Sequence
<220> FEATURE:
<223> OTHER INFORMATION: Linking peptide

<400> SEQUENCE: 10

Gln Thr Gly Gly
1
```